(12) United States Patent
Srouji et al.

(10) Patent No.: US 10,940,238 B2
(45) Date of Patent: Mar. 9, 2021

(54) MICROCAPILLARY NETWORK BASED SCAFFOLD

(71) Applicant: BONUS THERAPEUTICS LTD., Haifa (IL)

(72) Inventors: Samer Srouji, Haifa (IL); Shai Meretzki, Haifa (IL); Dror Ben-David, Kiryat Motzkin (IL)

(73) Assignees: BONUS THERAPEUTICS LTD., Haifa (IL); HEALTH CORPORATION OF GALILEE MEDICAL CENTER, Nahariya (IL)

( * ) Notice: Subject to any disclaimer, the term of this patent is extended or adjusted under 35 U.S.C. 154(b) by 0 days.

(21) Appl. No.: 15/759,940

(22) PCT Filed: Sep. 18, 2016

(86) PCT No.: PCT/IL2016/051032
§ 371 (c)(1),
(2) Date: Mar. 14, 2018

(87) PCT Pub. No.: WO2017/046804
PCT Pub. Date: Mar. 23, 2017

(65) Prior Publication Data
US 2018/0243477 A1  Aug. 30, 2018

Related U.S. Application Data

(60) Provisional application No. 62/220,129, filed on Sep. 17, 2015.

(51) Int. Cl.

| | |
|---|---|
| *A61L 27/46* | (2006.01) |
| *A61L 27/38* | (2006.01) |
| *A61L 27/56* | (2006.01) |
| *A61F 2/06* | (2013.01) |
| *A61L 27/44* | (2006.01) |
| *A61L 27/54* | (2006.01) |
| *A61L 27/58* | (2006.01) |
| *C12N 5/077* | (2010.01) |

(52) U.S. Cl.
CPC ............ *A61L 27/3804* (2013.01); *A61F 2/06* (2013.01); *A61L 27/446* (2013.01); *A61L 27/46* (2013.01); *A61L 27/54* (2013.01); *A61L 27/56* (2013.01); *A61L 27/58* (2013.01); *C12N 5/0652* (2013.01); *A61L 2430/02* (2013.01)

(58) Field of Classification Search
None
See application file for complete search history.

(56) References Cited

U.S. PATENT DOCUMENTS

| | | |
|---|---|---|
| 6,730,252 B1 | 5/2004 | Teoh et al. |
| 2007/0148139 A1 | 6/2007 | Vacanti et al. |
| 2010/0172952 A1 | 7/2010 | Srouji et al. |
| 2015/0328636 A1 | 11/2015 | Adams et al. |

FOREIGN PATENT DOCUMENTS

| | | |
|---|---|---|
| CN | 104888277 A | 9/2015 |
| WO | 2008041183 A2 | 4/2008 |

OTHER PUBLICATIONS

He et al., Journal of Biomedical Materials Research Part A (2008), pp. 205-216, published online May 19, 2008 (Year: 2008).*
McCullen et al., Biomed. Mater. vol. 4,(2009) pp. 1-9 (Year: 2009).*
Mercado-Pagan et al., Ann. Biomed Eng. Mar. 2015; 43(3): 718-729 (Year: 2015).*
Pham et al., Biomacromolecules, 2006, vol. 7, pp. 2796-2805 (Year: 2006).*
International Search Report PCT/IL2016/051032 Completed Dec. 28, 2016; dated Dec. 29, 2016 5 pages.
Written Opinion of the International Searching Authority PCT/IL2016/051032 dated Dec. 29, 2016 6 pages.

* cited by examiner

*Primary Examiner* — Scott Long
*Assistant Examiner* — Evelyn Y Pyla
(74) *Attorney, Agent, or Firm* — The Roy Gross Law Firm, LLC; Roy Gross

(57) ABSTRACT

A scaffold is provided, the scaffold comprising: at least one inlet tube; at least one outlet tube; and a plurality of porous elongated microtubes, wherein each one of said porous elongated microtube has an inner diameter of 5-100 micrometers, wherein said plurality of elongated microtubes extend from said at least one inlet tube to said at least one outlet tube and is in fluid communication thereto, Further provided is a method for producing and using the scaffold, such as for tissue engineering.

18 Claims, 27 Drawing Sheets

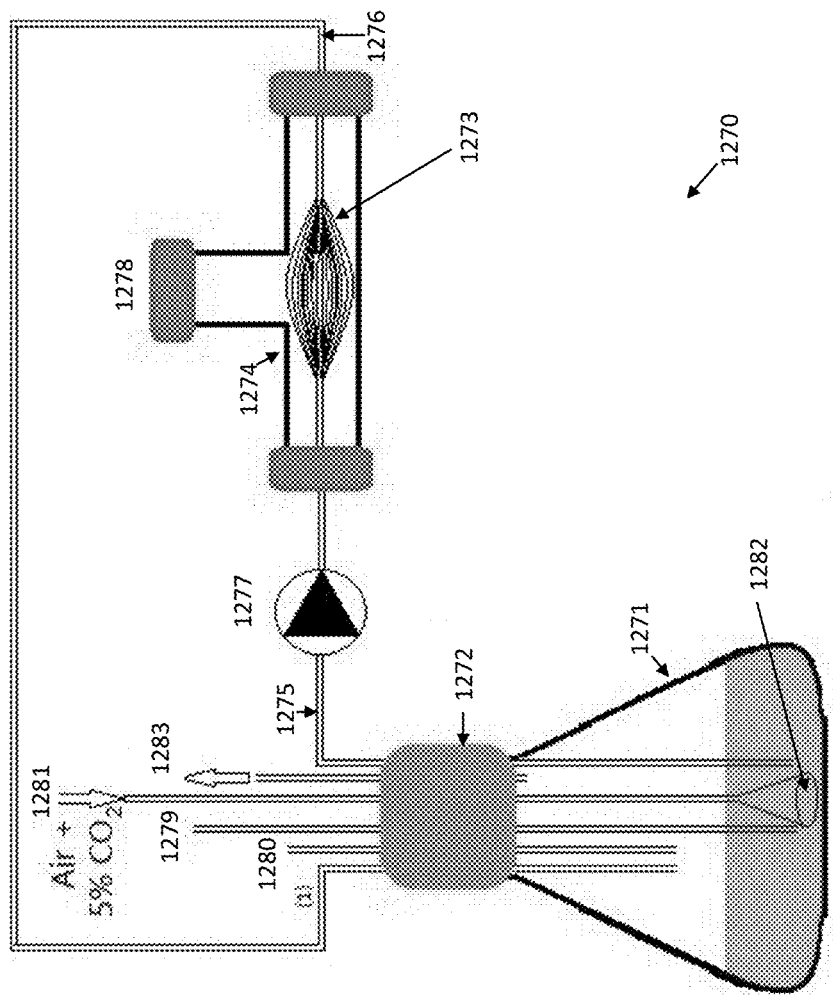
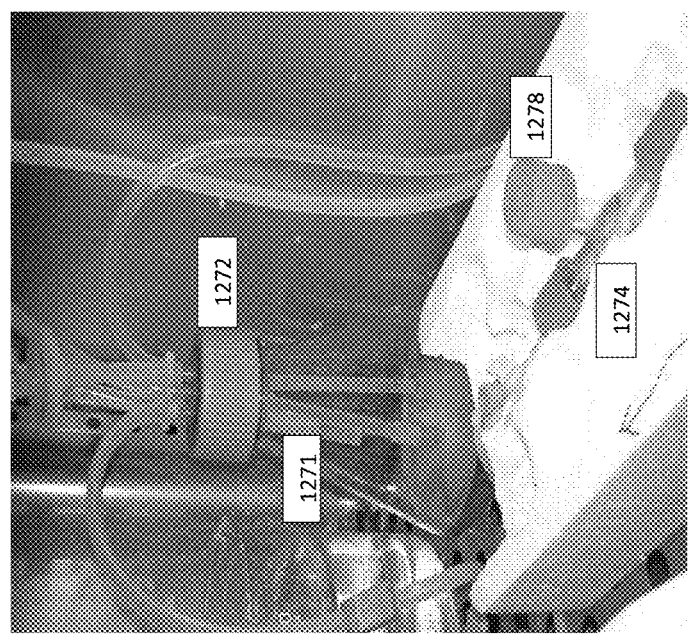
Fig. 12B
Fig. 12A

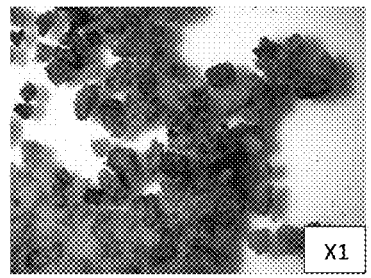
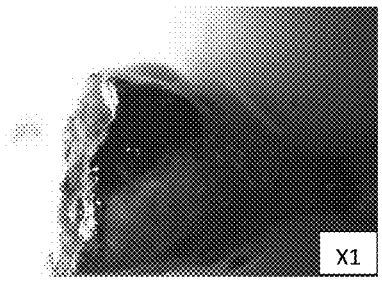
Fig. 13A                Fig. 13B
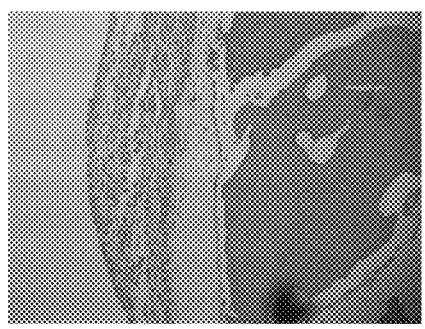
Fig. 14A                Fig. 14B
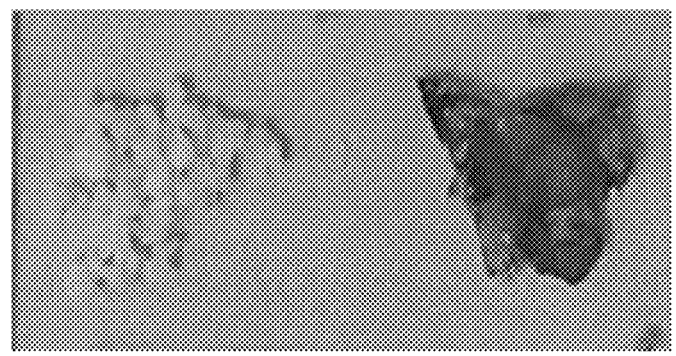
Fig. 15A        Fig. 15B

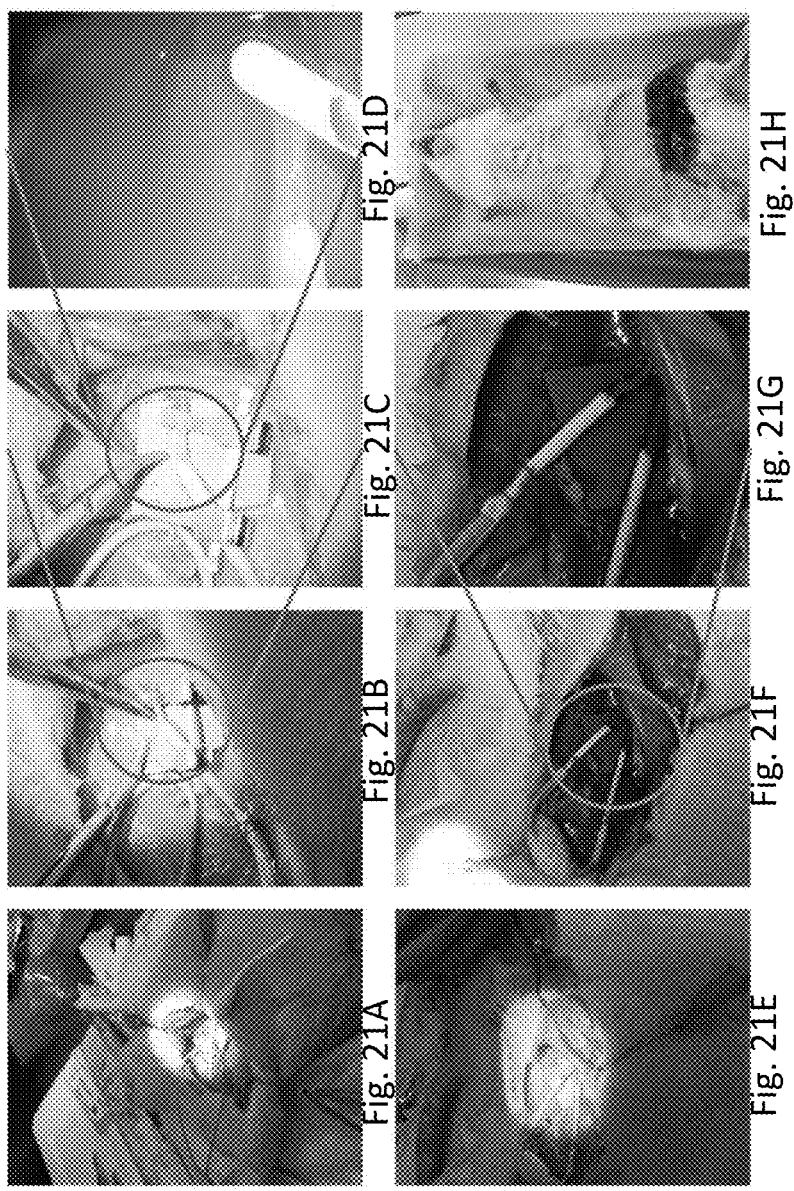

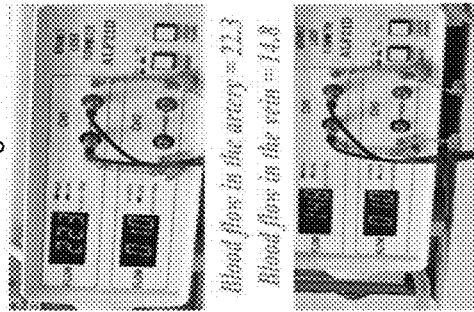
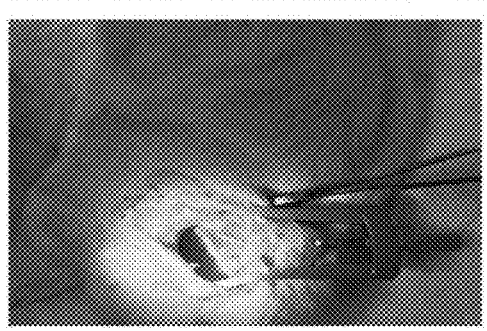
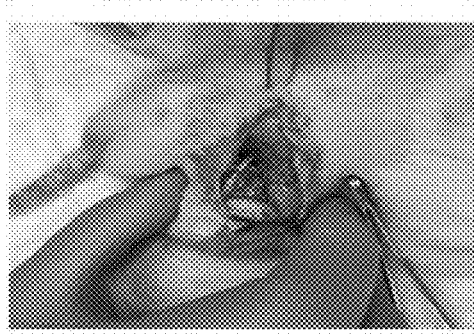
Fig. 23A  Fig. 23B  Fig. 23C  Fig. 23D  Fig. 23E

MICROCAPILLARY NETWORK BASED SCAFFOLD

CROSS-REFERENCE TO RELATED APPLICATIONS

This application is a National Phase of PCT Patent Application No. PCT/IL2016/051032 having International filing date of Sep. 18, 2016, which claims the benefit of priority U.S. Provisional Patent Application No. 62/220,129 filed on Sep. 17, 2015 entitled MICROCAPILLARY NETWORK BASED SCAFFOLD. The contents of the above applications are all incorporated by reference as if fully set forth herein in their entirety.

FIELD OF INVENTION

The present invention relates to the field of tissue engineering, and more particularly to the use of synthetic scaffold for the preparation of prosthetic implants.

BACKGROUND OF THE INVENTION

Tissue engineering techniques generally require the use of a scaffold as a three-dimensional template for initial cell attachment and subsequent tissue formation. As such, scaffold design is one of the most important aspects of tissue engineering. Appropriate selection of a scaffold is a key factor in the process of producing a viable and clinically relevant engineered tissue.

A scaffold is expected to possess the following characteristics for use in tissue engineering: (i) a three-dimensional porous structure that allows cell/tissue growth and flow transport of nutrients and metabolic waste; (ii) biodegradable or bioresorbable with a controllable degradation and resorption rate to match cell/tissue growth in vitro and/or in vivo; (iii) conducive surface chemistry for cell attachment, proliferation, and differentiation; (iv) mechanical properties to match those of the tissues at the site of implantation; and (v) process ability to form a variety of shapes and sizes for various applications.

In addition, in order to improve the survival and function of the implanted engineered tissue, adequate vascularization within the scaffold is crucial. Tissue vascularization is essential for delivery of nutrients (amino acids, glucose and oxygen) to the tissue and clearance of the metabolism byproducts from the tissue. Numerous techniques for development of vascularized tissue have recently emerged and are classified into two major categories: (a) vasculogenesis and angiogenesis-based techniques and (b) prevascularization-based techniques. The former are characterized by the ingrowth of newly formed blood vessels from the host microvasculature into the implanted engineered tissue and includes (1) micropatterning of vascular morphogenesis, (2) use of functionalized biomaterials to promote vasculogenisis and angiogenesis, (3) use of growth factor gradients and (4) co-culture of multiple cell types and control of cell-cell interactions. These techniques can be utilized to promote the formation of vascular networks in 3D engineered constructs in a regulated manner, but their central drawback lies in the time-consuming process of promoting vasculogenesis and angiogenesis, at a critical time when survival rates of implanted scaffolds are determined. The prevascularization-based techniques are founded on generating of preformed microvascular networks within tissue constructs prior to their implantation, which later further develop and interconnect with host blood vessels at the implantation site. The key advantage of these techniques is the capacity for immediate blood perfusion within the constructs upon implantation, which boosts the proliferation and growth of the cells. However, despite these advanced techniques, clinical use of engineered tissues and tissue substitutes is still largely restricted to avascular or thin tissues, and the marked progress achieved in small-scale tissue engineering applications in vitro was ultimately stalled due to the lack of vascular perfusion when scaled up to a sizes relevant for implantation and disease treatment.

Therefore, engineering a complex bulk tissue that can maintain its viability in vivo by transporting essential growth factors throughout the entire volume of the scaffold, remains an unmet need in the field of tissue engineering in general, and bone tissue engineering in particular.

SUMMARY OF THE INVENTION

According to a first aspect the invention provides a scaffold comprising:
  at least one inlet tube;
  at least one outlet tube; and
  a plurality of porous elongated microtubes, wherein each one of said porous elongated microtube has an inner diameter of 5-100 micrometers,
    wherein said plurality of elongated microtubes extend from said at least one inlet tube to said at least one outlet tube and is in fluid communication thereto.

In some embodiments, the scaffold further comprises a plurality of fibers having a diameter range of 0.5-10 micrometers. In some embodiments, the plurality of fibers is dispersed upon a portion of each of said plurality of porous elongated microtubes.

In some embodiments, the scaffold further comprises a plurality of bioactive particles embedded in between said plurality of fibers. In some embodiments, the scaffold further comprises a plurality of bioactive particles embedded in between said plurality of fibers and at least a portion of said porous elongated microtubes. In some embodiments, the bioactive particles have a range of 200-1500 micrometers in diameter.

In some embodiments, the plurality of bioactive particles comprises one or more type of osteoconductive particles. In some embodiments, the one or more types of the osteoconductive particles are selected from the group consisting of: calcium carbonate, hydroxyapatite (HA), demineralized bone material, morselized bone graft, cortical cancellous allograft, cortical cancellous autograft, cortical cancellous xenograft, tricalcium phosphate, corraline mineral and calcium sulfate. In some embodiments, the particles comprise hydroxylapatite (HA) and calcium carbonate.

In some embodiments, at least a portion of the scaffold is printed, molded, casted, polymerized, or electrospun. In some embodiments, at least one of said inlet tube, said outlet tube and said porous elongated microtubes are electrospun tubes. In some embodiments, said plurality of fibers are electrospun fibers. In some embodiments, the electrospun tubes or fibers comprise a polymer (or are formed from a polymeric solution) selected from the group consisting of: biodegradable polymers, non-biodegradable polymers and a combination thereof. In some embodiments, the polymer is selected from the group consisting of: polycaprolactone (PCL), polylactic acid (PLA), polyglycolic acid (PGA), and poly(Lactide-co-Glycolide) (PLGA), poly(orthoester), a poly(phosphazene), poly(or polycaprolactone, polyamide, polysaccharide, albumine and collagen.

In some embodiments, the inlet tube and the outlet tube have, independently, an inner diameter of range of 2,000-10,000 micrometers.

In some embodiments, the inlet tube and the outlet tube have, independently, a wall thickness range of 50-2,000 micrometers.

In some embodiments, the plurality of porous elongated microtubes have a wall thickness range of 0.5-50 micrometers.

In some embodiments, an average diameter of a pore of the plurality of porous elongated microtubes is 0.1-5 micrometers.

In some embodiments, the scaffold further comprises at least one agent for promoting cell adhesion, colonization, proliferation and/or differentiation. In some embodiments, the scaffold further comprises at least one agent for promoting cell adhesion selected from the group consisting of: gelatin, fibrin, fibronectin and collagen.

In some embodiments, the scaffold further comprises a plurality of cells. In some embodiments, the scaffold further comprises a plurality of cells seeded on and/or within the plurality of fibers. In some embodiments, the scaffold is adapted for cellular growth.

In some embodiments, the plurality of cells is selected from the group consisting of: adipose-derived stem cells, mesenchymal cells, mesenchymal stem cells, vascular smooth muscle cells, adipogenic cells, osteoprogenitors cells, osteoblasts, osteocytes, chondroblasts, chondrocytes and osteoclasts, endothelial progenitor cells, hematopoietic progenitor cells, micro vascular endothelial cells and macro vascular endothelial cells, beta cells, hepatocytes and a combination thereof.

According to another aspect, the invention provides a method of producing a tissue, the method comprising:
  providing a scaffold comprising:
    at least one inlet tube;
    at least one outlet tube; and
    a plurality of porous elongated microtubes, wherein each one of said porous elongated microtube has an inner diameter of 5-100 micrometers,
    wherein said plurality of elongated microtubes extend from said at least one inlet tube to said at least one outlet tube and is in fluid communication thereto;
  seeding cells on said plurality of porous elongated microtubes of said scaffold; and
  providing fluid (e.g., liquid) containing nutrients through said inlet of said scaffold, so as to provide nutrients from pores of said plurality of porous elongated microtubes to said cells;
  thereby producing said tissue.

In some embodiments, the scaffold further comprises a plurality of fibers dispersed upon each of said plurality of porous elongated microtubes. In some embodiments, the cells are seeded on and/or within said plurality of fibers.

In some embodiments, the tissue is suitable for being implanted into a subject in need thereof.

In some embodiments, the inlet and the outlet of the scaffold is suitable for being surgically connected to a vascular system of a subject in need thereof, thereby providing fluid communication between the subject's vascular system and said scaffold.

In some embodiments, the cells are selected from the group consisting of: adipose-derived stem cells, mesenchymal cells, mesenchymal stem cells, vascular smooth muscle cells, adipogenic cells, osteoprogenitors cells, osteoblasts, osteocytes, chondroblasts and osteoclasts, endothelial progenitor cells, hematopoietic progenitor cells, micro vascular endothelial cells and macro vascular endothelial cells, beta cells, hepatocytes and a combination thereof.

In some embodiments of the disclosed method, the scaffold further comprises plurality of bioactive particles embedded in between said plurality of fibers.

In addition to the exemplary aspects and embodiments described above, further aspects and embodiments will become apparent by reference to the figures and by study of the following detailed description.

BRIEF DESCRIPTION OF THE DRAWINGS

FIGS. 12A-B demonstrate a Hollow Fiber Reactor (HFR) system FIG. 12A is a photograph of a Hollow Fiber Reactor (HFR) system; and FIG. 12B is a schematic illustration of the Hollow Fiber Reactor (HFR) system (1280) of FIG. 12A;

FIGS. 13A-B show photographs following Giemsa staining of Coral particles from the inner side (A) and the outer side (B) of the HFR system;

FIGS. 14A-B show photographs following Hematoxylin & Eosin staining of HFR construct after one week of cultivation, magnification ×10, these photographs (A and B) demonstrate that the cells between the mineral particles were embedded within the PCL fibers, and generated organized connective tissue around and between the mineral particle;

FIGS. 15A-B show photograph following MTT staining of Mineral particles with live cells (A), and mineral particles without cells used as control (B);

FIGS. 21A-H are photographs demonstrating "End to End" anastomosis of vasculature-like system in SD rat using microsurgery technique: FIG. 21A shows exposure of femoral artery and vain before the microsurgery procedure, FIG. 21B shows "End to End" anastomosis of the microcapillary graft to the artery and vain vessels, FIG. 21C is a magnification of FIG. 21B, FIG. 21D is a magnification of FIG. 21C with focus on the connected microcapillary graft, FIG. 21E shows the microcapillary graft following the "end to end" anastomosis while the microcapillary graft is already connected and enables the blood circulation, FIG. 21F is a magnification of FIG. 21E, and FIG. 21G is a magnification of FIG. 21F, both focused on the "end to end" anastomosis area, and FIG. 21H shows the whole animal following stitching and closure of the surgery area;

FIGS. 23A-E are photographs demonstrating opening of the stitches (A) and exposure of the anastomosis site (B) performed one-day post transplantation to allow measurement of blood flow from artery to vein by laser Doppler (C), and the measured value for blood flow in the artery (D) and vein (E) as displayed on the laser flow meters;

FIGS. 26C-D are photographs demonstrating the measurement of blood flow through the transplant in anesthetized rats (C) and the measured value as displayed displayed on the laser flow meter (D);

DETAILED DESCRIPTION OF THE INVENTION

The present invention, in some embodiments, provides a 3-dimensional (3D) scaffold that supports growth of cells in a tissue construct, the scaffold comprises a porous tubular system that serves as a built-in vascular system. In some embodiments, the invention provides a scaffold comprising at least one inlet tube; at least one outlet tube; and a plurality of porous elongated microtubes, wherein each one of said porous elongated microtube has an inner diameter of 5-100 micrometers, and wherein said plurality of elongated microtubes extend from said at least one inlet tube to said at least one outlet tube and is in fluid communication thereto.

In some embodiments, the scaffold provides therein a tubular system facilitating transport of nutrients, gases and metabolites from liquid flux within the tubular system through the pores to cells attached thereto. In some embodiments, the scaffold's tubular system facilitates transport of by-products of metabolites from the cells.

The present invention is based in part on the finding that the scaffold of the invention serves as an adequate extracellular matrix (ECM) for cell integration, attachment, proliferation, growth and differentiation as a result of its structure.

In embodiments wherein the designated tissue is a bone, the scaffold may bear features required for effective bone-tissue engineered constructs and is characterized by osteoconductiveness that induces mesenchymal stem cells (MSC) differentiation into bone-forming cells. In some embodiments, the scaffold can serve as a bioreactor system providing appropriate growth conditions for MSC proliferation and differentiation into bone-forming cells in vitro and for their subsequent development into bone structure in vivo after anastomosis with host blood vessels.

Figure 1:
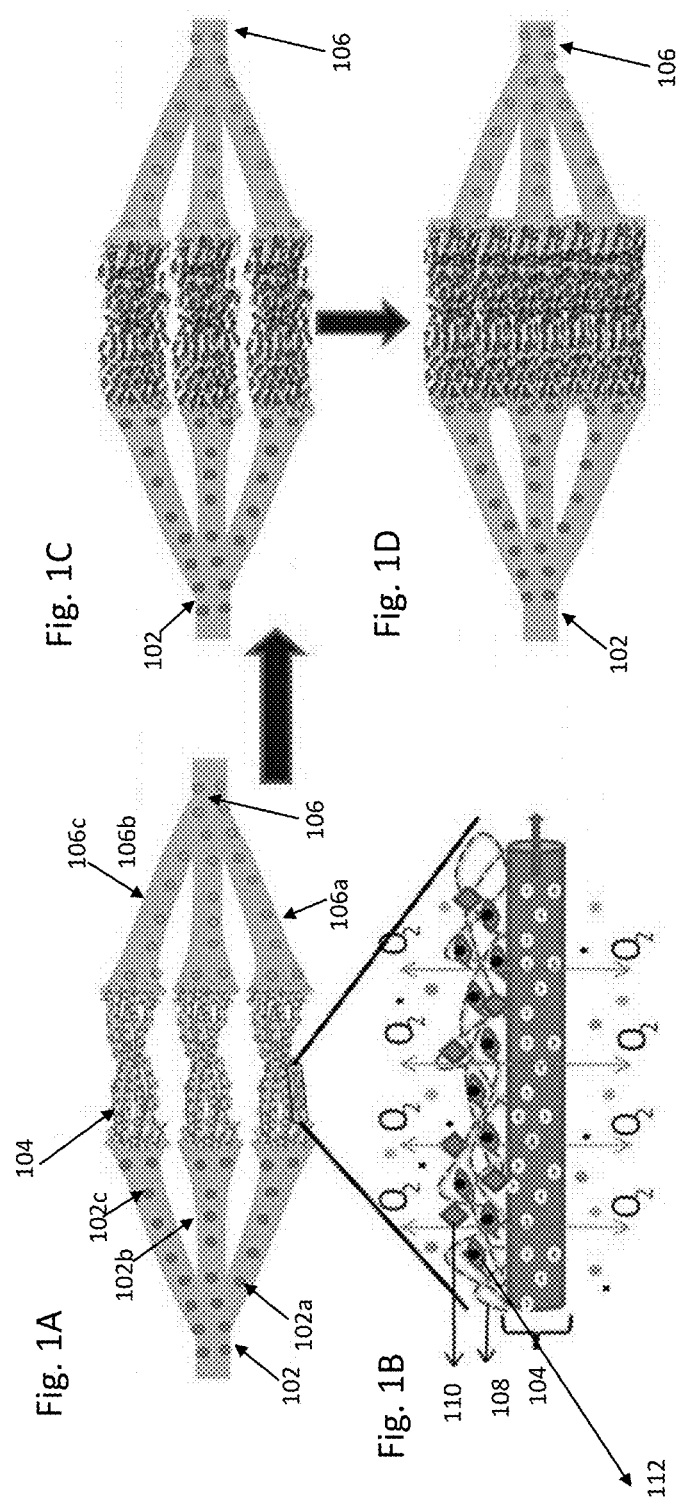
FIGS. 1A-D are schematic presentations of the microcapillary based scaffold.

Reference is now made to FIG. 1A, which is a schematic illustration of a scaffold 100 according to an embodiment of the invention. Scaffold 100 comprises an inlet tube 102 which is fluidly-connected to plurality of porous elongated microtubes 104 which extend in fluid communication to an outlet tube 106. Optionally, inlet tube 102 may consist of plurality of inlet tubes such as inlet tubes 102a, 102b, 102c. Optionally outlet tube 106 may consist of plurality of inlet tubes such as inlet tubes 106a, 106b, 106c. Reference is now made to FIG. 1B, which is an enlarged view of a section of porous elongated microtubes 104. A plurality of fibers 108 that may serve as a release system of angiogenic/growth factors are dispersed upon porous elongated microtubes 104. Optionally, bioactive particles 110 (e.g., osteoconductive particles) may be embedded within plurality of fibers 108. Optionally, a plurality of cells 112 may be seeded within plurality of fibers 108. For a non-limiting example, plurality of cells may include bone forming cells. The wide arrow depicts the flow of blood within porous elongated microtubes 104 and narrow arrows depict the flow of nutrients and oxygen ($O_2$) from porous elongated microtubes 104 to plurality of cells 112. FIGS. 1C-D illustrates forming of cell tissue upon porous elongated microtubes 104.

Scaffold

According to another aspect, the present invention provides a scaffold comprising: at least one inlet tube; at least one outlet tube; and a plurality of porous elongated microtubes, wherein each one of said porous elongated microtube has an inner diameter of 5-100 micrometers, and wherein said plurality of elongated microtubes extend from said at least one inlet tube to said at least one outlet tube and is in fluid communication thereto.

In some embodiments, the diameters of the inlet and/or outlet tubes is 2-1000, or 200-1000, or 2-100 folds greater than the diameter of the porous elongated microtube. In some embodiments, the inlet tube and the outlet tube have an inner diameter range of 2,000-10,000 micrometers. In some embodiments the inlet tube and the outlet tube have a wall thickness range of 50-2,000 micrometers. In some embodiments the plurality of porous elongated microtubes has a wall thickness range of 0.5-50 micrometers. In some embodiments the ratio between the number of porous elongated microtubes and any one of the inlet and outlet tubes is in the range of 1:1-10:1, or alternatively 1:1-5:1, or alternatively 1:1-3:1, or alternatively 1:1-50:1, or alternatively 1:1-100:1.

The term "porous" as used herein relates to a plurality of openings, pores, or holes that may be filled (permeated) by water, air or other materials. In some embodiments, pores are not permeable to cells such as mammalian cells. In some embodiments, a diameter of a pore is less than 10 micrometers. In some embodiments, a diameter of a pore is between 0.1-5 micrometers. In some embodiments, a diameter of a pore is between 0.1-10 micrometers, between 0.5-5 micrometers, or alternatively between 1-10 micrometers.

As used herein throughout, the term "fluid communication" means fluidically interconnected, and refers to the existence of a continuous coherent flow path from one of the components of the system to the other if there is, or can be established, liquid and/or gas flow through and between the ports, when desired, to impede fluid flow therebetween.

In some embodiments, the scaffold further comprises a plurality of fibers having a diameter range of 0.5-10 micrometers, or 0.1-20 micrometers, or 1-5 micrometers. In some embodiments, the fibers, or at least some of the fibers may be hollow. In some embodiments, a distance between adjacent fibers ranges between 20 micrometers and 300 micrometers. In some embodiments the fibers are arranged in a mesh. In some embodiments, the mesh comprises openings defined between adjacent fibers. In some embodiments, the openings have a diameter range of 20 micrometers and 300 micrometers. In some embodiments the plurality of fibers and/or the mesh is dispersed upon at least a portion of the scaffold. In some embodiments, the plurality of fibers and/or the mesh is dispersed upon a portion of each of said plurality of porous elongated microtubes.

The term "scaffold" as used herein refers to a porous, artificial, three-dimensional structure comprising biocompatible material that provides a surface suitable for adherence and proliferation of cells. Biocompatible, as used herein, is intended to describe materials that, are non-toxic to cells in vitro and upon administration in vivo, do not induce undesirable long-term effects. As used herein the term "in vitro" refers to any process that occurs outside a living organism. As used herein the term "in-vivo" refers to any process that occurs inside a living organism.

As used herein, the term "diameter" refers to the largest linear distance between two points on the surface of a described element (e.g., tube, fiber, openings). The term "diameter", as used herein, encompasses diameters of spherical elements as well as of non-spherical elements.

In some embodiment, the scaffold is biodegradable. Biodegradable, as used herein, is intended to describe materials that are biologically degraded in vivo.

Scaffold of the present invention, or a portion thereof may be printed, molded, casted, polymerized, or electrospun.

In some embodiments, the scaffold contains or consists of electrospun material (e.g. macro micro or nanofibers).

In some embodiments the scaffold may consists of, or include, one or more polymers selected from the group consisting of: biodegradable polymers and non-biodegradable polymers. In some embodiments the scaffold may consists of or include any of the following materials: polycaprolactone (PCL), polylactic acid (PLA), polyglycolic acid (PGA), poly(Lactide-co-Glycolide) (PLGA), poly(orthoester), a poly(phosphazene), a polyamide, a polysaccharide, albumin, collagen (e.g., collagen I or IV), fibrin, hyaluronic acid, poly(vinyl alcohol) (PVA), Polyhydroxybutyrate (PHB), poly(ethylene oxide) (PEO), fibrin, polydioxanone (PDO), trimethylene carbonate (TMC), polyethyleneglycol (PEG), alginate, chitosan copolymers or mixtures thereof.

In some embodiments, the scaffold further comprises bioactive agents. As used herein, the terms "bioactive" is used to refer to any effect on, interaction with, or response from living cells and/or tissue. The term "bioactive agent" refers to a molecule that exerts an effect on a cell or tissue.

Representative examples of types of bioactive agents include therapeutics, vitamins, electrolytes, amino acids, peptides, polypeptides, proteins, carbohydrates, lipids, polysaccharides, nucleic acids, nucleotides, polynucleotides, glycoproteins, lipoproteins, glycolipids, glycosaminoglycans, proteoglycans, growth factors, differentiation factors, hormones, neurotransmitters, prostaglandins, immunoglobulins, cytokines, and antigens. Various combinations of these molecules can be used. Examples of cytokines include macrophage derived chemokines, macrophage inflammatory proteins, interleukins, tumor necrosis factors. Examples of proteins include fibrous proteins (e.g., collagen, elastin) and adhesion proteins (e.g., actin, fibrin, fibrinogen, fibronectin, vitronectin, laminin, cadherins, selectins, intracellular adhesion molecules, and integrins). In various cases, the bioactive agent may be selected from fibronectin, laminin, thrombospondin, tenascin C, leptin, leukemia inhibitory factors, RGD peptides, anti-TNFs, endostatin, angiostatin, thrombospondin, osteogenic protein-1, bone morphogenic proteins, osteonectin, somatomedin-like peptide, osteocalcin, interferons, and interleukins. In some embodiments, the bioactive agent includes a growth factor, differentiation factor, or a combination thereof.

As used herein, the term "growth factor" refers to a bioactive agent that promotes the proliferation of a cell or tissue. Representative examples of growth factors that may be useful include transforming growth factor-α (TGF-α), transforming growth factor-β (TGF-β), platelet-derived growth factors (PDGF), fibroblast growth factors (FGF), nerve growth factors (NGF) including NGF 2.5s, NGF 7.0s and beta NGF and neurotrophins, brain derived neurotrophic factor, cartilage derived factor, bone growth factors (BGF), basic fibroblast growth factor, insulin-like growth factor (IGF), vascular endothelial growth factor (VEGF), EG-VEGF, VEGF-related protein, Bv8, VEGF-E, granulocyte colony stimulating factor (G-CSF), insulin like growth factor (IGF) I and II, hepatocyte growth factor, glial neurotrophic growth factor (GDNF), stem cell factor (SCF), keratinocyte growth factor (KGF), transforming growth factors (TGF), (e.g., TGFs α, β, β1, β2, and β3), any of the bone morphogenic proteins, skeletal growth factor, bone matrix derived growth factors, and bone derived growth factors and mixtures thereof.

As used herein the term "differentiation factor" refers to a bioactive agent that promotes the differentiation of cells. Representative examples include neurotrophins, colony stimulating factors (CSF), and transforming growth factors. Some growth factors may also promote differentiation of a cell or tissue. Some differentiation factors also may promote the growth of a cell or tissue. For example, TGF may promote growth and/or differentiation of cells. In some embodiments, the scaffold comprises at least one bioactive agent for promoting cell adhesion, colonization, proliferation and/or differentiation. In some embodiments, the at least one agent for promoting cell adhesion is selected from the group consisting of: gelatin, fibrin, fibronectin and collagen.

The bioactive agent may be incorporated into the scaffold in a variety of different ways. In one embodiment, the bioactive agent is located and/or formulated for controlled release to affect the cells or tissues in or around the oriented nanofiber structures. For instance, it may be dispersed in a controlled release matrix material. In one embodiment, the bioactive agent is provided in lipid microtubules or nanoparticles selected to modulate the release kinetics of the bioactive agent. Such particles may be dispersed among the nanofibers, or provided within the scaffold. In another embodiment, the bioactive agent is actually integrated into, forms part of, the tubes, microtubes and/or fibers themselves. This may be done, for example, by adding the bioactive agent to a polymer solution prior to electrospinning the solution to form the tubes, microtubes and/or fibers themselves. Release of the bioactive agent may be controlled, at least in part, by selection of the type and amounts of biodegradable matrix materials in the nanoparticles or nanofibers.

In some embodiments the scaffold further comprises cells such as endothelial cells attached thereto within one or more the tubes or microtubes of the scaffold. One skilled in the art will appreciate that incorporation of endothelial cells within tubes of the scaffold may enhance vascular tissue formation, e.g., so as to replace the scaffold's synthetic vascular tubes/microtubes which are degraded in vivo.

In some embodiments, the scaffold further comprises plurality of bioactive particles having a range of 200-1500 micrometers in diameter. In some embodiments, particles of the invention are larger than 1 micrometer in diameter. Particles of the invention may have any shape or form (e.g., spherical, triangular, rectangular, etc.). In some embodiments, the particles are embedded within the scaffold. In some embodiments, the particles are embedded in between the plurality of fibers dispersed upon the scaffold or a portion thereof.

In some embodiments, the bioactive particles are ceramic particles. As used herein, the term "ceramic" is intended to refer to an inorganic, nonmetallic material, typically crystalline in nature, though it could be amorphous as well. Ceramics generally may be compounds formed between metallic and nonmetallic elements, such as, for example, aluminum and oxygen (e.g., alumina—$Al_2O_3$), calcium and oxygen (e.g., calcia—CaO), silicon and oxygen (e.g., silica—$SiO_2$) and other analogous oxides, nitrides, borides, sulfides, and carbides as well as carbon matrices. However, "ceramic", as used herein, should not be unduly construed as being limited to a ceramic body in the classical sense, that is, in the sense that it consists entirely of inorganic materials, but rather refers to a body which is predominantly ceramic with respect to either composition or dominant properties.

In some embodiments, the plurality of particles comprises one or more type of osteoconductive particles. As used in here "osteoconductive" refers to the ability of a substance to serve as a suitable template or substance along which bone may grow. In one embodiment, the one or more types of the osteoconductive particles are osteoconductive ceramic particles selected from the group consisting of: calcium carbonate, hydroxyapatite (HA), demineralized bone material, morselized bone graft, cortical cancellous allograft, cortical cancellous autograft, cortical cancellous xenograft, tricalcium phosphate, coralline mineral and calcium sulfate. In some embodiments, the bioactive particles comprise hydroxylapatite (HA) and calcium carbonate.

Applications

A scaffold according to the present invention can be used for a wide variety of applications. Embodiments of the scaffolds disclosed herein are suitable for uses such as for cell culture and cell transplantation. In some embodiments the scaffold may serve as a bioreactor system providing appropriate growth conditions for cells in vitro. In some embodiments, the scaffold may serve as perfusion bioreactor that provides for immediate supply of nutrients and gases to cells grown in a tissue culture.

Reference is now made to FIG. 12B which is a schematic illustration of a hollow fiber reactor (HFR) system 1270 comprising a scaffold (also referred to as microcapillary system) 1273, according to an embodiment of the invention. Scaffold 1273 is connected to an inlet tube 1275 and an outlet tube 1276. Optionally, inlet tube may be equipped with a peristaltic pump 1277 to facilitate constant circulation of a growth medium. Optionally, the circulation of growth medium facilitates a turbulence movement of the growth medium. Scaffold 1273 is enclosed within a HFR vessel 1274. The HFR system may further include a medium reservoir 1271. Optionally, medium reservoir 1271 is equipped with a cap 1272. Optionally, inlet tube 1275 and outlet tube 1276 which are connected to scaffold 1270 contact medium reservoir 1271 via ports (not shown) in cap 1272. Optionally, waste removal is done using a waste outlet 1279 via a port (not shown) in cap 1272. Optionally, growth medium replenishment is done using a feed inlet 1280 via a port (not shown) in cap 1272. Optionally, system 1270 is continuously aerated through aeration inlet 1281 with filtered air/$CO_2$ (95%/5%, respectively) gas mixture bubbling out through a sparger 1282 dipped into the growth medium. Optionally, pressure is release through an output 1283. Optionally, cell seeding is conducted through an HFR inoculation port 1278. Following cell seeding onto scaffold 1273, inoculation port 1278 is closed and during closed system is maintained during the 3D growth phase of the cells. In some embodiment, the flow rate of the growth medium is regulated. In some embodiments, the required flow rate of growth medium is determined according to the characteristics of the scaffold (e.g. diameter). In some embodiment, the RPM of pump 1277 motor is used as the main control of the flow rate. For a non-limiting example, when using a microcapillary system including a capillary tube, which has a diameter of 0.5 mm, connected at each side to a one of two vein like tubes having a diameter of 0.86 mm the required RPM is between 10 and 50. As exemplified in example 10 the required flow rates and RPM may be calculated (i.e. by applying equations 2-4) for specific applications.

The term "bioreactor" as used herein means any apparatus, which provides biologically active, protected environment suitable for cultivation of cells. The term "perfusion bioreactor" as used herein means a fluidized-bed reactor for cell culture designed for continuous operation as a perfusion system, i.e., a system in which fresh medium is fed to the bioreactor at the same rate as spent medium is removed. In some embodiments, the scaffold is implantable, and may be surgically connected to a subject's blood vessels. In some embodiments the scaffold may serve as a bioreactor system providing appropriate growth conditions for cells in vitro and for their subsequent development into bone structure in vivo after anastomosis with host blood vessels. As used herein, the term "anastomosis" refers to the joining together of two hollow structures, for a non-limiting example, two arteries or veins, to achieve continuity. An anastomosis can be end-to-end, side-to-side, or end-to-side depending on the circumstances of the required reconstruction or bypass procedure.

In some embodiments, the scaffold is used to produce a tissue. In some embodiments the method for producing a tissue comprises: providing the scaffold of the invention, seeding cells on said plurality of porous elongated microtubes of said scaffold; and providing liquid containing nutrients through said inlet of said scaffold, so as to provide nutrients from pores of said plurality of porous elongated microtubes to said cells; thereby producing the tissue.

In some embodiments, the method comprises a preliminary step of determining a desired flow rate of said liquid containing nutrients through said scaffold. In some embodiments, the desired flow rate is suitable for producing a tissue. In some embodiments, the desired flow rate is suitable for the step of cells seeding. In some embodiments, the desired flow rate is suitable for the step of cells culturing. In some embodiments, the flow rate is controlled by a pump. In some embodiments, an RPM range of the pump is determined according to a desired flow rate.

The term "subject" as used herein refers to an animal, more particularly to non-human mammals and human organism. Non-human animal subjects may also include prenatal forms of animals, such as, e.g., embryos or fetuses. Non-limiting examples of non-human animals include: horse, cow, camel, goat, sheep, dog, cat, non-human primate, mouse, rat, rabbit, hamster, guinea pig, pig. In one embodiment, the subject is a human. Human subjects may also include fetuses. In one embodiment, a subject in need thereof is a subject afflicted with a fractured bone, a bone injury, diminished bone mass and/or bone abnormality.

The terms "liquid", "fluid" and "media" as used interchangeably herein refer to water or a solution based primarily on water such as phosphate buffered saline (PBS), or water containing a salt dissolved therein. The term aqueous medium can also refer to a cell culture medium. The term "cell culture medium" refers to any liquid medium which enables cells proliferation. Growth media are known in the art and can be selected depending of the type of cell to be grown. For example, a growth medium for use in growing mammalian cells is Dulbecco's Modified Eagle Medium (DMEM) which can be supplemented with heat inactivated fetal bovine serum.

The term "nutrients" may include but is not limited to fats, glucose, mono- or oligo-saccharides, minerals, trace elements and/or vitamins. Nutrients may further include one or more gaseous components such as primarily oxygen and carbon dioxide. Nutrients may further include one or more metabolite.

The term "metabolite" or "metabolites" as used herein designates compounds that are naturally produced by an organism (such as a plant or animal) and that are directly involved in the normal growth, development or reproduction of the organism. This includes, but is not limited to, any compound produced by plant or animal cells, or genetically modified plant or animal cells, such as proteins or other types of chemical compounds.

The terms "cell" and "cells" as used herein, refer to isolated cells, cell lines (including cells engineered in vitro), any preparation of living tissue, including primary tissue explants and preparations thereof. Any type of cell can be added to the scaffold for culturing and possible implantation, including cells of the muscular and skeletal systems, such as chondrocytes, fibroblasts, muscle cells and osteocytes, parenchymal cells such as hepatocytes, pancreatic cells (including Islet cells), cells of intestinal origin, and other cells such as nerve cells and skin cells, either as obtained from donors, from established cell culture lines, or even before or after genetic engineering. Pieces of tissue can also be used, which may provide a number of different cell types in the same structure. The scaffold can also be used as a three-dimensional in vitro culture system for attachment-dependent cells, e.g., hepatocytes in a 3D micro environment which mimics the physiological micro environment more closely. In some embodiments, cells are selected from the group consisting of: adipose-derived stem cells, mesenchymal cells, mesenchymal stem cells, vascular smooth muscle cells, adipogenic cells, osteoprogenitors cells, osteoblasts, osteocytes, chondroblasts, chondrocytes and osteoclasts, endothelial progenitor cells, hematopoietic progenitor cells and a combination thereof.

Scaffolds or portions thereof described herein can be used to generate synthetic organs or tissues or portions thereof, including but not limited to, respiratory tissues (e.g., tracheal, bronchial, esophageal, alveolar, and other pulmonary or respiratory tissues), circulatory tissues (e.g., arterial, venous, capillary, and other cardiovascular tissue, for example, heart chambers of other heart regions or heart or cardiac valves or valve structures), renal tissue (for example renal pyramids of the kidney), liver tissue, cartilaginous tissue (e.g. nasal or auricular), bone tissue, skin tissue, and any other tissue or organ or portion thereof that is being engineered on a synthetic scaffold.

In some embodiments, the cells may be allowed to proliferate on the scaffold for a time period, in which the cells can grow to form colonies, after which the colonies can fuse to form a network of cells, and subsequently forming a tissue. Generally, the time for proliferation can range from a few hours or days to a few weeks, such as about 1 day to about 4 weeks, or about 1 day to about 2 weeks, or about 1 day to about 1 week, or about 1 day to about 4 days. The time for proliferation can also depend on the cultivation conditions for the cells. Parameters of the cultivation condition can include, for example, temperature, pH, amount of water, pressure, nutrients present, and type of cell. Cultivation conditions of cells are known in the art and can therefore be adapted by a person skilled in the art depending on the desired cell type and application.

The term "tissue" refers to a structure formed by related cells joined together, wherein the cells work together to accomplish specific functions. An organ refers to a differentiated structure of an organism composed of various cells or tissues and adapted for a specific function. Therefore, one or more species of living cells can be added into the mixture to form a specific organ. For a non-limiting example, the heart which is an organ contains muscle tissue that contracts to pump blood, fibrous tissue that makes up the heart valves and special cells that maintain the rate and rhythm of heartbeats.

As used herein, the term "seeding" refers to plating, placing and/or dropping the cells of the present invention into the electrospun scaffold of the present invention. It will be appreciated that the concentration of cells which are seeded on or within the electrospun scaffold depends on the type of cells used and the composition of the scaffold.

Electrospun Scaffold

In some embodiments, at least a portion of the scaffold is produced by electrospinning. In some embodiments, portions produced by electrospinning may be connected such as by epoxy glue.

As used herein, the term "electrospinning" refers to a technology which produces electrospun fibers (e.g. nanofibers) from a polymer solution. During this process, one or more polymers are liquefied (i.e. melted or dissolved) and placed in a dispenser. An electrostatic field is employed to generate a positively charged jet from the dispenser to the collector. Thus, a dispenser (e.g., a syringe with metallic needle) is typically connected to a source of high voltage, preferably of positive polarity, while the collector is grounded, thus forming an electrostatic field between the dispenser and the collector. Alternatively, the dispenser can be grounded while the collector is connected to a source of high voltage, preferably with negative polarity. As will be appreciated by one ordinarily skilled in the art, any of the above configurations establishes motion of positively charged jet from the dispenser to the collector. Reverse polarity for establishing motions of a negatively charged jet from the dispenser to the collector is also contemplated. At the critical voltage, the charge repulsion begins to overcome the surface tension of the liquid drop. The charged jets depart from the dispenser and travel within the electrostatic field towards the collector. Moving with high velocity in the inter-electrode space, the jet stretches and the solvent therein evaporates, thus forming fibers which are collected on the collector forming the electrospun scaffold.

In some embodiments, the inner diameter and wall thickness of the tubes are adjusted by changing the collecting mandrels and controlling the deposition time of electrospinning, respectively. In some embodiments, the porosity of a porous tube correlates with fiber diameter and polymer weight concentration, which enable manipulation of the scaffold porosity by changing the polymer weight concentration. In some embodiments, a porous scaffold produced by electrospinning exhibits permeability within the permeability range for human trabecular bone as exemplified below (permeability constant K=10-10-10-12 [m2]). In some embodiments, Cell adherence is supported by the high surface area-to-volume ratios of the electrospun nanofibers, whose nanoscale architectures expose the cells to more binding sites compared with micro- and macro-scale architecture, and by that lead to a better adherence of every cell by allowing its attachment to multiple nanofibers.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

In the discussion unless otherwise stated, adjectives such as "substantially" and "about" modifying a condition or relationship characteristic of a feature or features of an embodiment of the invention, are understood to mean that the condition or characteristic is defined to within tolerances that are acceptable for operation of the embodiment for an application for which it is intended. Unless otherwise indicated, the word "or" in the specification and claims is considered to be the inclusive "or" rather than the exclusive or, and indicates at least one of, or any combination of items it conjoins.

It should be understood that the terms "a" and "an" as used above and elsewhere herein refer to "one or more" of the enumerated components. It will be clear to one of ordinary skill in the art that the use of the singular includes the plural unless specifically stated otherwise. Therefore, the terms "a," "an" and "at least one" are used interchangeably in this application.

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

In the description and claims of the present application, each of the verbs, "comprise," "include" and "have" and conjugates thereof, are used to indicate that the object or objects of the verb are not necessarily a complete listing of components, elements or parts of the subject or subjects of the verb. Other terms as used herein are meant to be defined by their well-known meanings in the art.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Additional objects, advantages, and novel features of the present invention will become apparent to one ordinarily skilled in the art upon examination of the following examples, which are not intended to be limiting. Additionally, each of the various embodiments and aspects of the present invention as delineated herein above and as claimed in the claims section below finds experimental support in the following examples.

EXAMPLES

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference. Other general references are provided throughout this document.

Materials and Methods:
Electrospinning of Fibrous Tubes

A 9% solution of polycaprolactone (PCL, Mw 80,000 Da; Sigma-Aldrich) in a 80:20 (w/w) mixture of chloroform (Frutarom) and dimethylformamide (DMF, Frutarom) was electrospun using the following parameters: an applied voltage of 12 kV, a flow rate of 2.5 ml/hour and a tip-collector distance of 12-17 cm. PCL fibrous tubes were collected using a rotating aluminum wire with a diameter of either 0.5 mm or 2.8 mm, at 350 rpm. The collected tubes were then dried in a vacuum, at a pressure of ~10-3 atm, and then stored in a desiccator at relative humidity of ~30%.

Capillary Design

Figure 2:
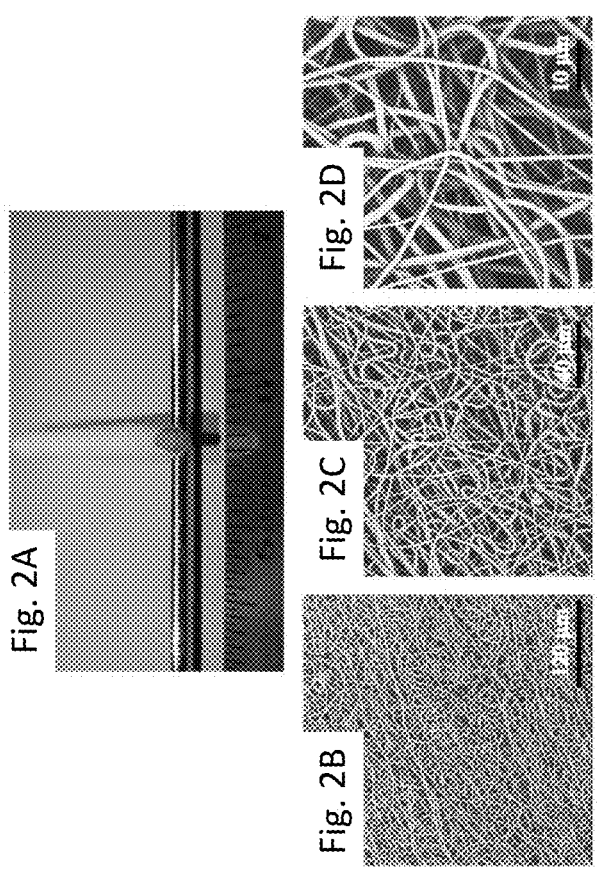
FIGS. 2A-D are optical images of (A) an electrospun capillary, (B-D) PCL electrospun fibers (9 wt. %).

Tubular scaffolds with an inner diameter of 2 mm, wall thickness of 0.2 mm±0.02 mm and a length of 25 mm, were successfully constructed (FIG. 2a). Inner diameter and wall thickness of electrospun tubular scaffolds can be adjusted by using mandrels with different external diameters and by controlling the electrospinning deposition time, respectively. The design may be adjusted according to a desired application. SEM images of the electrospun scaffolds are shown in FIGS. 2b-d. All scaffolds showed randomly oriented fibers and interconnected pore structure throughout the scaffold. However, fiber diameter and pore size were distinct. To quantify the permeability of the scaffolds, different air pressure drop through 10×10×0.1 mm³ layers of scaffolds was applied and the total pressure drop (dP) was measured using a commercially available water manometer. Permeability was calculated using Equation 1.

$$v = -\frac{k}{\mu_a} \cdot \frac{dP}{dx} \qquad \text{Equation 1}$$

where v is the flux (discharge per unit area, with units of length per time[m/s]), dP/dx is the pressure gradient vector (Pa/m), and $\mu_a$ is the air viscosity (Pa·s).

Fabrication of the Complex Scaffold

Figure 4A:
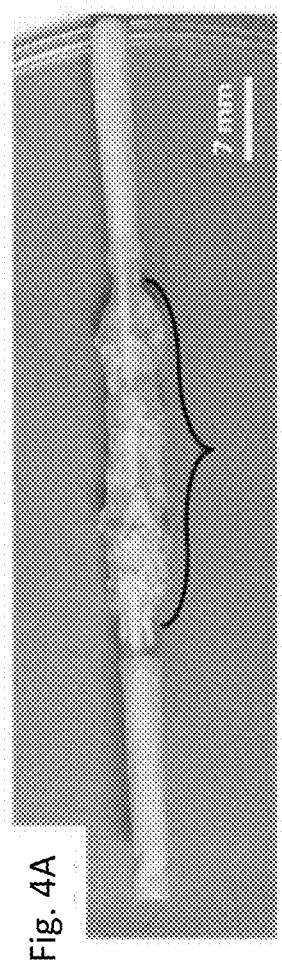
FIGS. 4A-D present images of the complex scaffold: (A) the complex scaffold: Pro-Osteons dispersed on and in between the PCL-electrospun tubes. The indicated region is the region that is seeded with cells, (B) the vasculature-like system: made of PCL-electrospun tubes, (C-D) a cross-sectional view of the vasculature-embedded scaffold, showing three PCL tubes surrounded with layers of Pro-Osteon particles and PCL fiber.
Figure 4B:
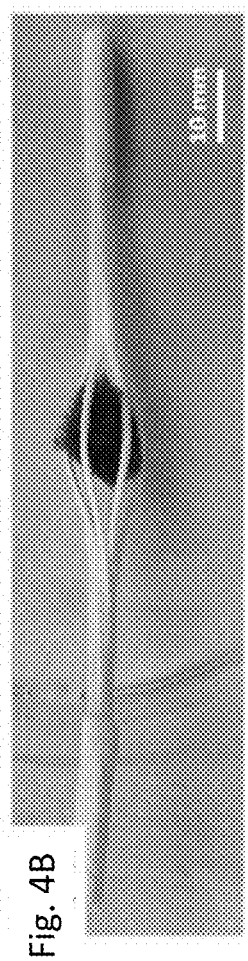
Figure 4C:
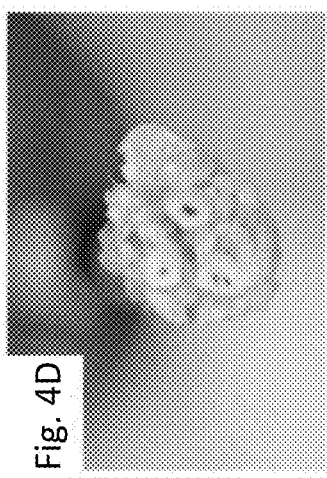
Figure 4D:
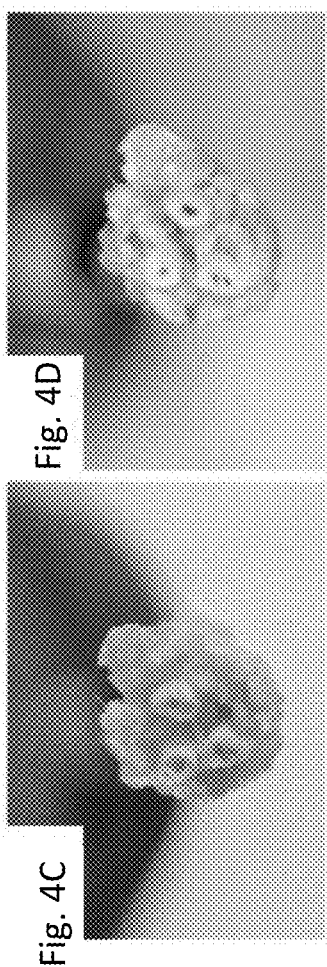
Figure 5C:
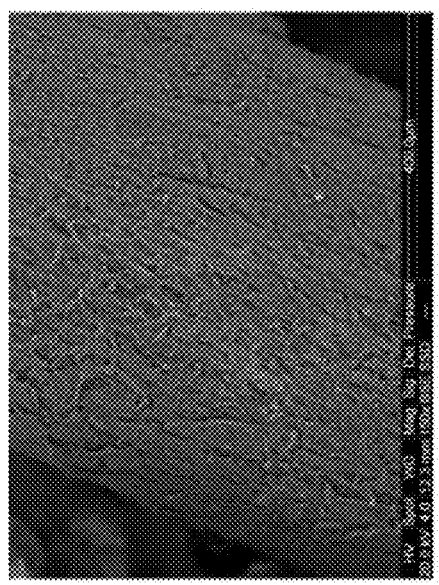
FIGS. 5A-C present SEM images of the complex scaffold: (A) cross section of the complex scaffold showing the PCL fibers and the Pro-Osteon particles dispersed on and in between the PCL-electrospun tubes, (B) the scaffold bulk including Pro-Osteon particles and electrospun PCL fibers, (C) electrospun PCL tube (different magnifications (×50, ×40 & ×150) are shown)
Figure 5B:
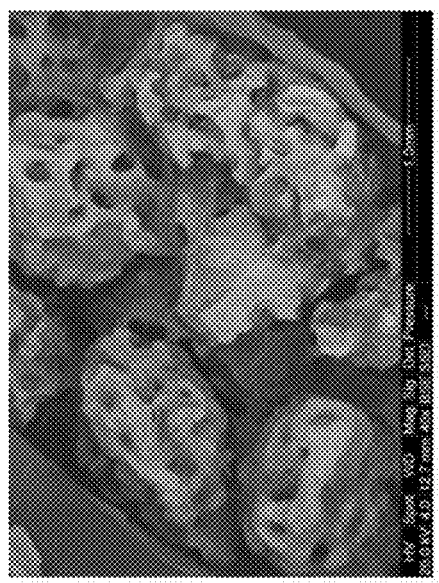
Figure 5A:
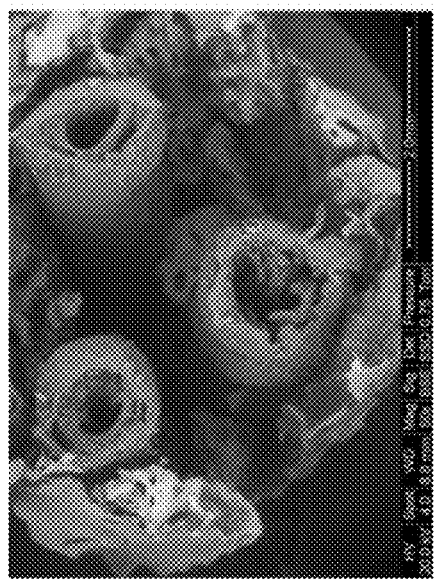

The complex scaffold is composed of a vasculature-like system embedded in a bulk scaffold. The vasculature-like system is comprised of electrospun PCL tubes, whereas the bulk surrounding scaffold includes bone-inducing material (Pro-Osteon particles of 0.5-1 mm diameter, Bepex) and electrospun PCL fibers (FIGS. 4 & 5a). Using a wet brush, the Pro-Osteon particles are dispersed in between and on the PCL tubes and are kept in place by the PCL fibers that also are dispersed around the tubes and Pro-Osteon (FIGS. 4a & 5b). Each vasculature structure consists of three or more small electrospun PCL tubes (inner diameter. 0.5 mm, FIG. 5c), connected together from both sides by another electrospun PCL tube with a diameter of 2.8 mm (FIG. 4b). The latter tubes resemble inlet and outlet grafts for media infusion into the construct. The small tubes tips are inserted into the large one and connected to it using an epoxy adhesive that forms a liquid-tight adherence. The radius of the entire scaffold system is adjusted to ~1 cm. All experiments were performed 3 or 4 times at least, and more, if necessary. All data are expressed as mean±standard deviation (SD).

Example 1

Preliminary Capillary Design

As mentioned in the method section, inner diameter and wall thickness of electrospun tubular scaffolds can be adjusted. The average fiber diameter and pore size increased as a function of the PCL weight concentration in the electrospun polymer solution. More specifically, the mean diameter of fibers electrospun from the low concentration (8 wt. %) PCL solution was 200 nm±65 nm, while for the higher PCL solution concentration (11 wt. %) mean fiber diameter was 550 nm±45 nm. As expected, the porosity of the electrospun scaffold is correlated with the fiber diameter, namely, higher porosity was observed in scaffolds with fibers of larger diameter. Additionally, the permeability of the scaffolds was quantified using Darcy equation, and the Darcy constant k was found to be in the range of $10^{(-10)}$-$10^{(-12)}$ [m²].

Example 2

Preliminary Flow and Permeability Study Using Homemade Bioreactor

Figure 3:
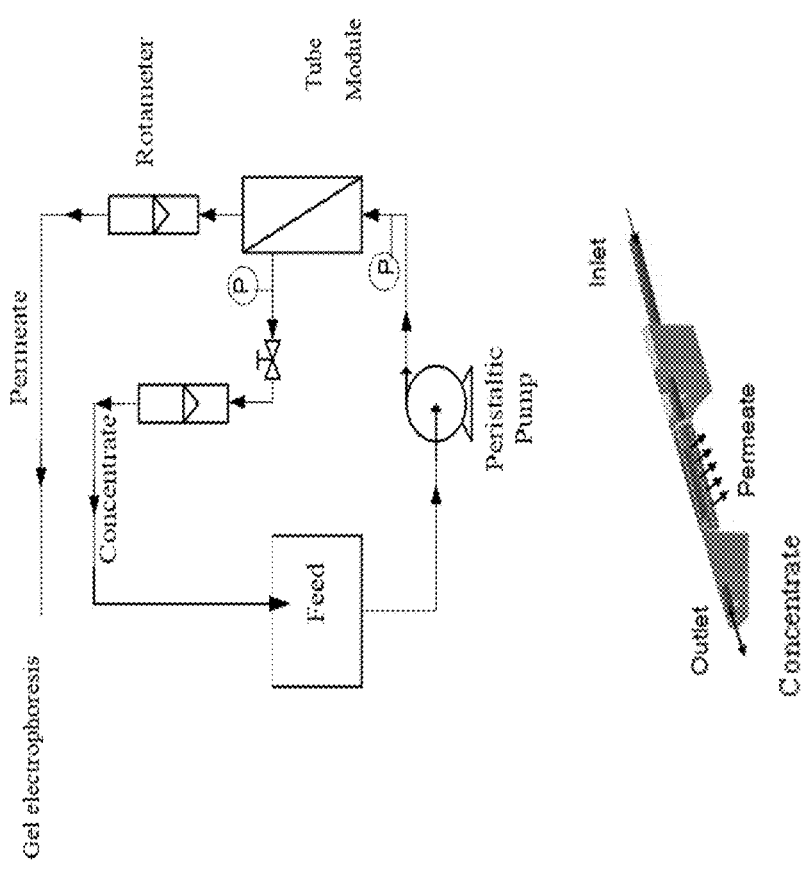
FIG. 3 is a schematic illustration of a permeation testing setup of an electrospun tube connected to inlet/outlet.

Flow and tube wall permeability were characterized by tube assembly in a homemade bioreactor. The tube was connected to an inlet and outlet (FIG. 3) and immersed in a PBS bath (Invitrogen). A 10% solution of fetal calf serum (FCS) serum in PBS (Invitrogen) was pushed through the tube using a peristaltic pump, while the longitudinal pressure was regulated, in the range of 1-2 N/m2, with a valve close to the outlet. The serum that passed through the PCL wall tubes (the permeate) entered the surrounding bath and the excess fluid (concentrate) exited and collected in the feed reservoir (FIG. 3). The permeate was collected during the experiment and protein concentration was measured using a native 10% gel electrophoresis system.

Figure 7A:
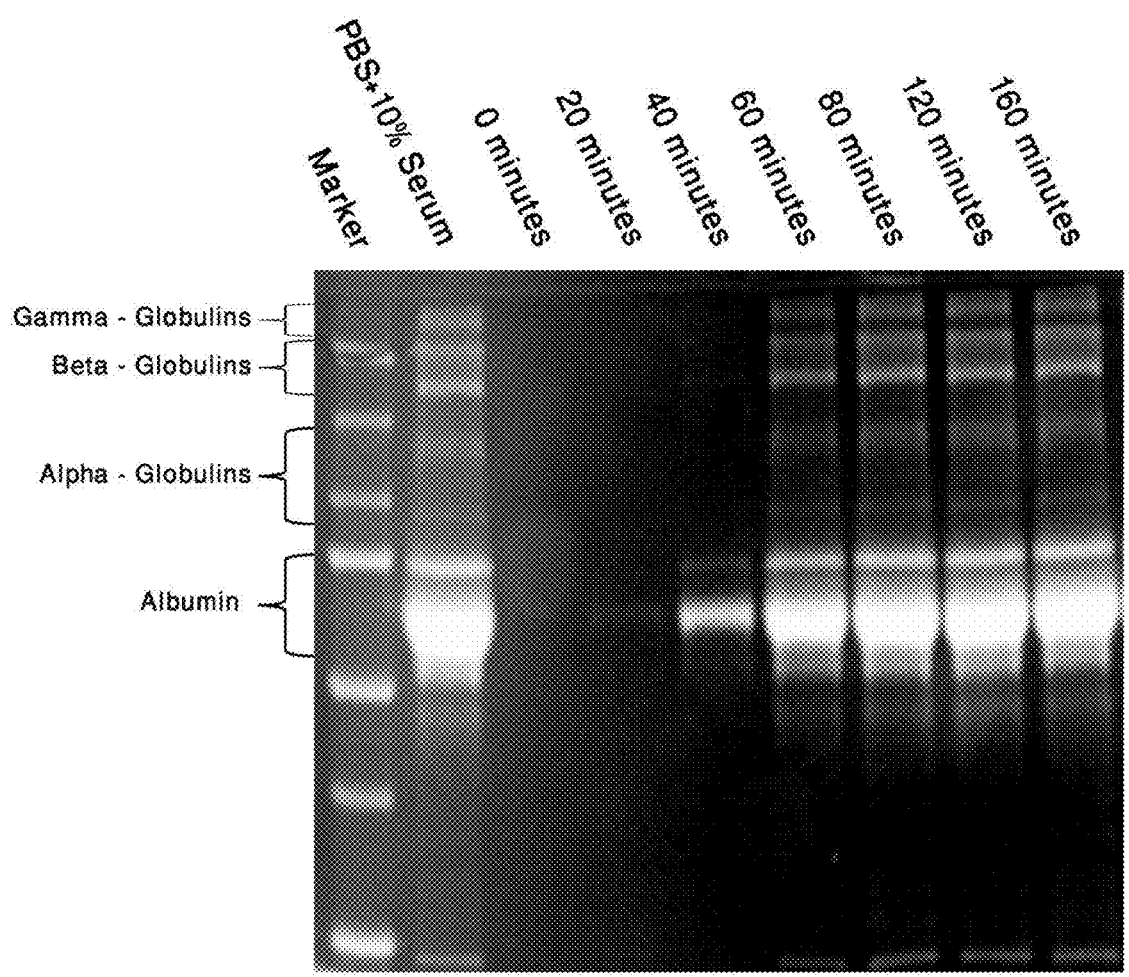
FIGS. 7A-C present gel electrophoresis results: (A) the proteins that passed through the PCL tubes walls and into the PBS bath, (B) quantification of the protein bands observed on the gel, (C) increase of protein concentrations in the inner PBS bath.
Figure 7B:
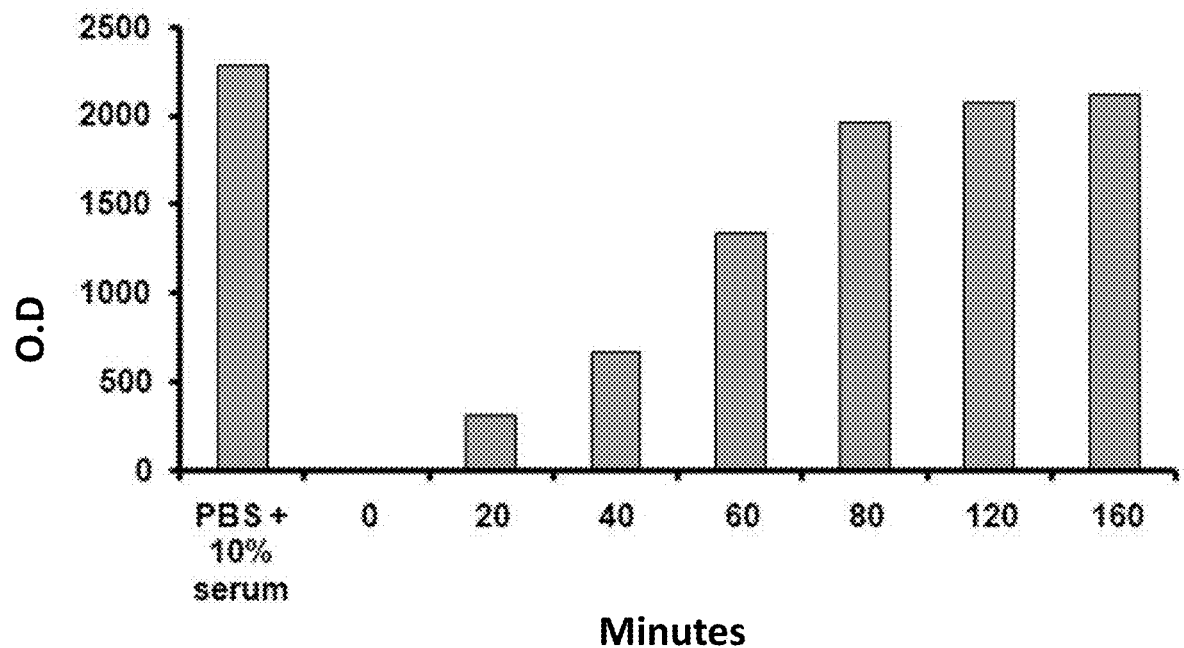
Figure 7C:
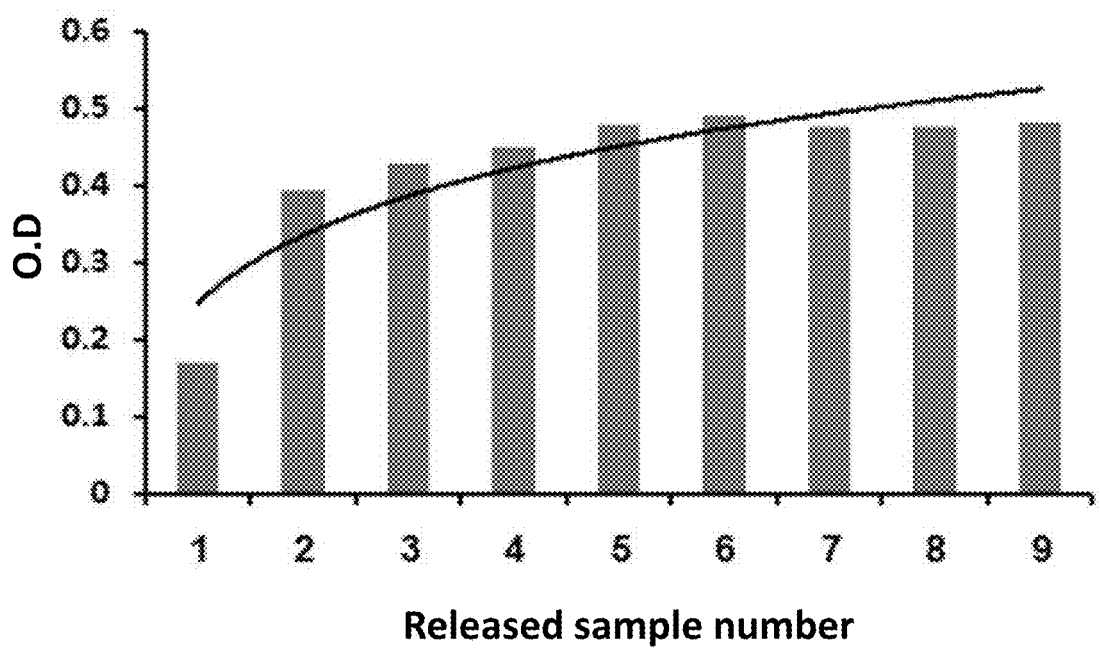

The PCL tubes proved permeable, as demonstrated from the increasing protein concentrations measured over time in the PBS bath in which perfused tubes were immersed (FIGS. 7A-C). The system reached saturation within 120 minutes of perfusion. The tubes were permeable to all protein sizes present in the serum.

Example 3

Preliminary Adjustment of Culture Conditions

Human adipose-derived mesenchymal stem cells (MSCs) were isolated from human adipose tissue explants (1-2 mm$^3$) extracted from abdominal area. This study was approved by the the Rambam Health Care Campus Helsinki Committee (#0370-12-RMB). The explants were placed in fibronectin-coated flasks and incubated in a basic growth medium, containing Dulbecco's Modified Eagle Medium (DMEM) supplemented with 10% fetal bovine serum (FBS), 1% L-glutamine and 1% Pen-strep antibiotics (all from Biological Industries) for 5-7 days. After one week, adipose tissue explants were washed and MSCs were trypsinized. MSCs were cultured in a basic growth medium, which was changed once in 3 days. Cells were expanded up to passage 3 or 4 in growth medium and were then used in in vitro and in vivo studies.

Inductive conditions were achieved by culturing MSCs in inductive medium comprised of DM, supplemented with 10% FBS, $10^{-8}$ M dexamethasone and 100 μg/ml L-ascorbic acid 2-phosphate sesquimagnesium (both from Sigma Aldrich). Moreover, osteogenic differentiation was induced by culturing the cell-seeded scaffolds in osteoconductive medium comprised of inductive medium further supplemented with 10 mM β-glycerophosphate (Sigma Aldrich).

MSCs were only seeded onto scaffold regions containing Pro-Osteons (FIG. 2a). The seeding region dimensions were approximately 2.2 cm long and 1 cm wide. Prior to seeding, all scaffold samples were soaked in 70% ethanol for sterilization and washed several times with phosphate buffered saline (PBS). One million of trypsin-released cells were counted and re-suspended in $50_11.1$ growth or inductive medium and were seeded onto the scaffold. The cell-seeded samples were then incubated for 70 min with slow rotation, and then re-suspended in growth or inductive medium, respectively.

Proliferation of MSCs Cells in a Static Culture:

To evaluate the proliferation rates and growth viability of the isolated MSCs, the Alamar blue-based viability assay was used. Cells were seeded on the scaffolds and cultured in growth medium for 28 days. Cell viability was assessed on days 1, 3, 7, 14, 21 and 28 post-seeding. At each time point, the cell-seeded scaffold was washed twice in PBS and incubated for 2 hours in medium containing 10% Alamar blue reagent (Serotec, UK). The fluorescence of Alamar blue reagent was recorded by FLUOstar galaxy fluorescence reader (BMG Labtech, Germany) at 540 nm excitation and 580 nm emission.

Figure 6:
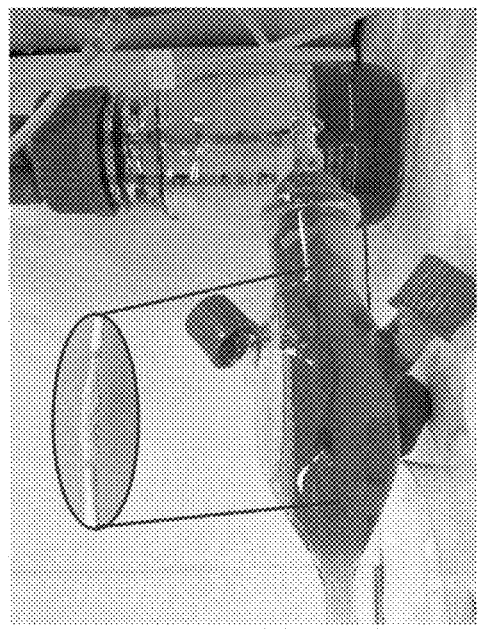
FIG. 6 shows the complex scaffold connected to a medium-flow bioreactor.

Histological Analysis of Cell-Seeded Scaffolds Cultured Under Dynamic Conditions:

MSCs were seeded on the complex scaffolds (~1 million cells per scaffold) and cultured for two weeks in a medium flow bioreactor system (FIG. 6). During the first week, the cells were cultured in inductive medium, before being transferred to osteoconductive conditions. For histological staining, cell-seeded scaffolds were fixed in 10% neutral buffered formalin (NBF) for 48 hours, and then decalcified in 10% ethylenediaminetetraacetic acid (EDTA) solution for 1 week. The constructs were then embedded in paraffin after undergoing standard fixation. Transverse, 5 μm-thick sections were placed on silanized slides for hematoxylin & eosin (H&E) or Masson's Trichrome staining.

Morphological Analysis of Cell-Seeded Complex Scaffolds Cultured Under Dynamic Conditions:

MSCs were seeded on complex scaffolds, which were then cultured in growth medium for approximately 1 month in a medium flow bioreactor system. Samples were then fixed in 10% NBF, dehydrated in graded ethanol solutions and soaked in hexamethyldisilazane for 15 minutes. The samples were then sputter-coated with gold and characterized using a Phenom desktop scanning electron microscope (SEM) (5 kV accelerating voltage, FEI Company).

Static Culture Conditions

Figure 8:
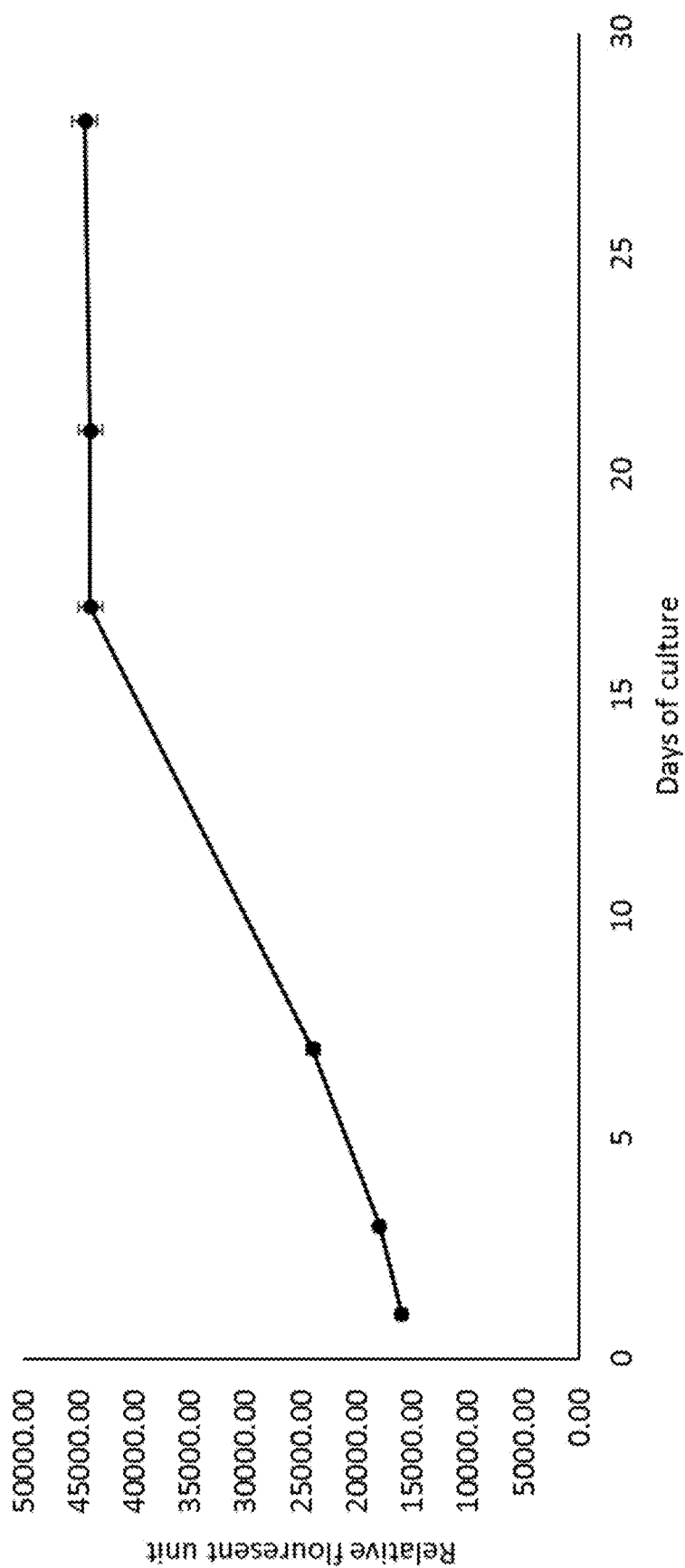
FIG. 8 is a graph showing cells proliferation when cultured on complex scaffolds under static conditions. The Alamar blue-based viability assay showed increase of proliferation rates of MSCs in correlation to the culture days. Error bars are the standard deviation (SD) collected from three samples.
Figure 9:
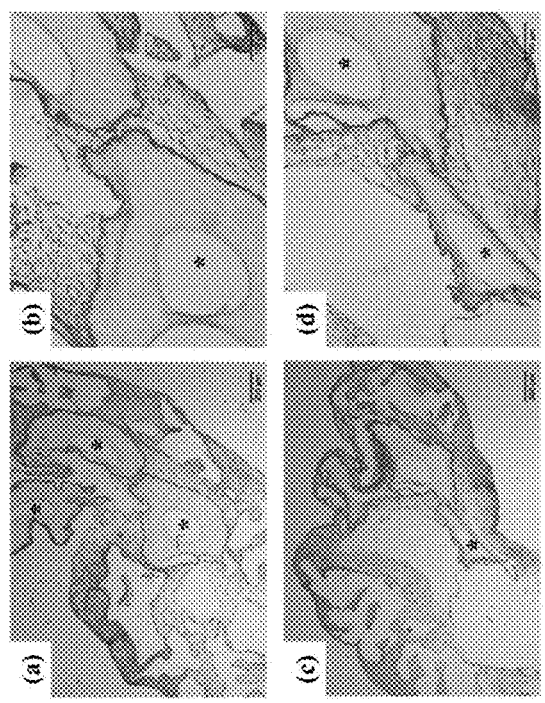
FIGS. 9A-D show H&E-stained histological sections of the MSC-seeded complex scaffolds. Complex scaffolds were seeded with MSCs, and cultured under static conditions for one week and then in dynamic conditions for an additional week before being fixed and stained. Different magnifications are shown: (A, C) ×4, (B, D) ×10. The PCL tubes are indicated by asterisks.

The metabolic activity rate and proliferation capacities of MSCs cultured on complex scaffolds under static conditions increased in direct correlation with the duration of culture, as presented in FIG. 8. This result is a preliminary indication of the effective biological support provided by the complex scaffold.

Dynamic Culture Conditions

After examining the biocompatibility of the scaffold in a static culture, it was tested in a dynamic culture. An MSC-embedded complex scaffold was first cultured for one week under static conditions and then transferred for an additional week in an inductive medium, delivered via a medium flow bioreactor system (FIG. 6). The scaffold was then fixed, decalcified, embedded in paraffin and stained. The H&E-stained histological sections (FIGS. 9A-D of the seeded scaffold, illustrate the complex structure of the scaffold that consisted of three PCL tubes embedded within a bulk tissue (asterisks indicate the tubes). The images also demonstrated the extensive MSC proliferation and the expansion within the scaffold. It was also noted that MSCs did not penetrate the PCL tubes, but rather, settled on the wall of the tubes.

Figure 10:
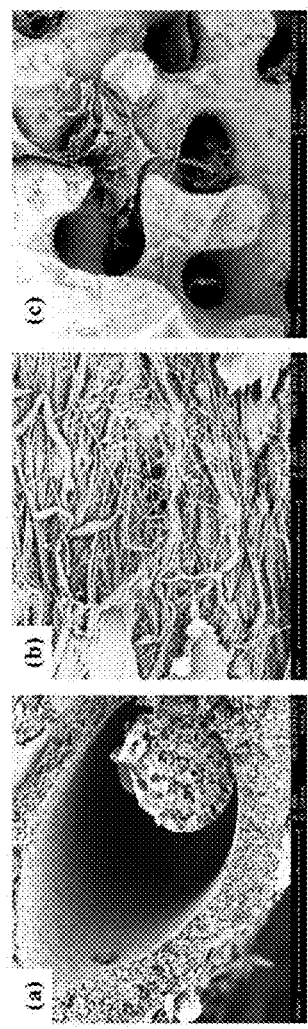
FIGS. 10A-C show SEM images of the MSC-seeded complex scaffold grown under dynamic conditions: (A) cross-section of a PCL tube showing the integration of cells along the tube walls, (B-C) cells were distributed on and in between the PCL fibers and Pro-Osteon particles (different magnifications (×450, ×2680 and ×415) are shown)

The SEM analysis corroborated these findings (FIGS. 10A-C), as well as excellent integration of the cells within the scaffold. Cells were distributed along and in between the osteoconductive particles, depositing their extracellular matrix components throughout the bulk part of the scaffold. In addition, cells were observed along the external walls of the embedded tubes. It is important to state that in contrast to histological sections, wherein the ceramics are dissolved through a decalcification process, the Pro-Osteon particles can still be seen in the SEM analysis.

Example 4

Preliminary Implantation of MSC-Seeded Scaffolds in Ectopic Models

In order to examine the biocompatibility of the complex scaffolds in vivo, they were seeded with induced cells and then implanted in ectopic animal models.

On the implantation day, complex scaffolds were seeded with cells that were previously cultured for at least 10 days in inductive medium. Prior to implantation, a fibrin clot, composed of 1:1 rat fibrinogen: rat thrombin (Sigma Aldrich), was added to the cell-seeded constructs to stabilize the sample.

All surgical processes described below were performed following the protocols approved by the Institutional Animal Care and Use Committee. Three groups of 6-week-old, nude female mice (n=5 per group, Harlan Laboratories) were anesthetized using a 0.5:0.5:9 ketamine:xylazine:PBS cocktail at a dose of 400 μL/20 g, delivered with a 25-gauge needle. Cell-seeded complex constructs were subcutaneously implanted to the dorsum of the anesthetized mice. In parallel, unseeded scaffolds and seeded Pro-Osteons particles were subcutaneously implanted as negative and positive controls, respectively. Tissue samples of the construct area were extracted for histological analysis 8 weeks post-implantation.

Figure 11:
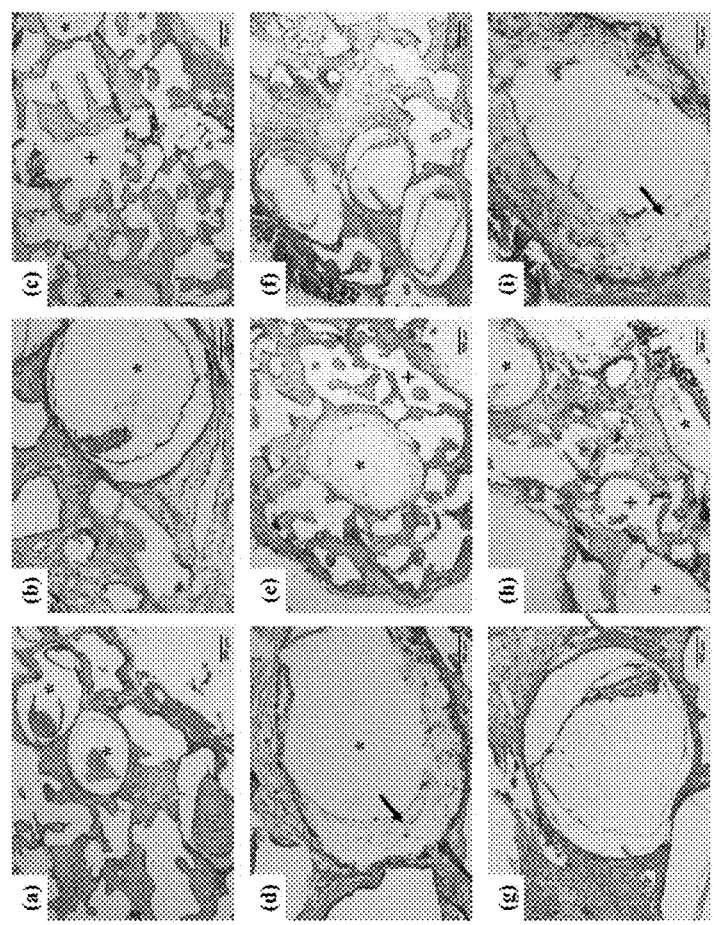
FIGS. 11A-I show H&E- and Trichrome-stained histological sections of the implanted MSC-embedded complex scaffold in animal models. Cell-seeded scaffolds were implanted in an ectopic animal model in order to examine their biocompatibility. Eight weeks later, the implanted scaffolds were extracted and histological sections were prepared and stained with H&E staining and Trichrome staining. PCL tubes, PCL fibers and Pro-Osteon particles are indicated by black asterisks, arrows and crosses, respectively. Blood vessels, muscle tissue and collagen accumulation are noted by arrows, different magnifications are shown: (A, C, E, F and H) ×4, (B, D, G and I) ×10.

Histological sections of the implanted scaffolds extracted 8 weeks after implantation, showed the new formed tissues around the Pro-Osteons (crosses represent their position before decalcification; FIGS. 11C, E and H) and the vasculature-like system within the implanted scaffold, represented by three PCL electrospun-tubes (asterisks; FIGS. 11A, F and H). Moreover, the PCL fibers that constitute the tubes wall (black arrows; FIGS. 11D and I), MSC integration within the scaffold (black dots examining the cells' nuclei), formation of blood vessels (red arrows; FIGS. 11B, F, G and H) and muscle tissue (yellow arrows; FIGS. 11A and F) and accumulation of collagen into the scaffold (blue arrows; FIGS. 11B, F and G) were observed. Furthermore, maintained structural integrity of vasculature-like scaffold was apparent and no inflammatory reaction toward the graft was detected, indicating its biocompatibility with the host.

Example 5

A Custom Designed Hollow Fiber Reactor (HFR) System for Dynamic Culturing

A hollow fiber reactor (HFR) (1270) was developed for use with the microcapillary system to enable cell growth and differentiation prior to transplantation. The bioreactor system (FIGS. 12 A and 12B) is based on 500 ml Erlenmeyer flask used as a medium reservoir (1271); it has a specially designed cap (1272) that contains inlets and outlets for feed, waste and aeration. The microcapillary system (1273) is placed into the HFR vessel (1274), connected to an inlet tube (1275) and an outlet tube (1276) and then the growth medium is constantly circulated throughout the system. Cell seeding is conducted using the HFR inoculation port (1278). Following cell seeding onto microcapillary system (1273), it is closed and during all of the 3D growth phase maintains closed system parameters.

Seeding Conditions:

8-12×10$^6$ MSCs in 300 ul growth medium were injected onto the construct (using the inoculation port of the HFR) in several points on the construct and incubated at static conditions for adequate cell adherence. Following 20 minutes, 2 ml growth medium was added and incubation continued at static conditions (37° C., 5% CO2) for total of 120 minutes. After the incubation, the HFR vessel was connected to the system tubing and the growth medium (total volume of 150 ml) circulation through the microcapillary construct began (at 18 RPM based on preliminary studies). The circulating medium was aerated by air+5% CO2 mix into the medium reservoir using a sparger (aeration rate is 15 ml/hour). Medium change (50 ml) was performed twice a week using the waste and the feed ports on the cap. The bioreactor system was very stable and was able to run during a long period (one month was successfully tested). Osteogenic induction was performed for two days by adding BMP2 (150 ng/ml final conc.) to the growth medium.

Example 6

Cells Characterization Following Culturing of MSCs on the Microcapillary Scaffold in the HFR Dynamic System Compared to a Static System a. Cell Attachment and Growth on the Microcapillary Scaffold:

Since cell counting on the microcapillary scaffold is challenging, cells growth and construct coverage is shown using Giemsa staining, which demonstrates the MSCs growth onto the microcapillary system (FIGS. 13A and B, magnification ×1).

Histological evaluation (Hematoxylin & Eosin staining) after one week of culturing in the HFR system supports MSCs growth onto the scaffolds construct. As can be seen in the images (FIGS. 14A and B), the cells between the mineral particles, embedded within the PCL fibers, have generated organized connective tissue around and between the mineral particles.

Cells viability was demonstrated by MTT staining (FIGS. 15A and B). The live cells are violet colored (15A) and the control mineral particles (without cells) are not colored (15B). This method demonstrates cells coverage as well as viability.

b. Osteogenic Potential of MSCs Following Osteogenic Induction by BMP-2, in Static and Dynamic Growth Systems:

In order to evaluate the MSCs osteogenic potential following cultivation in the HFR system experiments ending with osteogenic induction of the cultured cells were performed. The experiments compared static and dynamic (HFR) growth systems. The static system is composed of a petri dish or in an Erlenmeyer in which cells are cultured on the microcapillary scaffold and medium is manually replaced. The dynamic system is composed of a fully closed bioreactor which enables medium aeration and flow along and within the microcapillary graft, as well as an automatic medium replacement by specific ports.

Figure 16A:
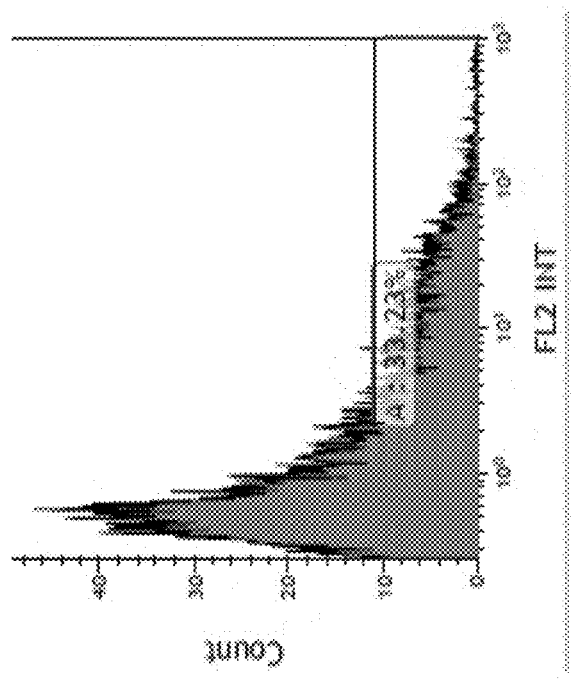
FIGS. 16A-B are graphs showing FACS results for the osteogenic marker ALP from MSCs grown in a Static HFR system (A) and dynamic HFR system (B).
Figure 16B:
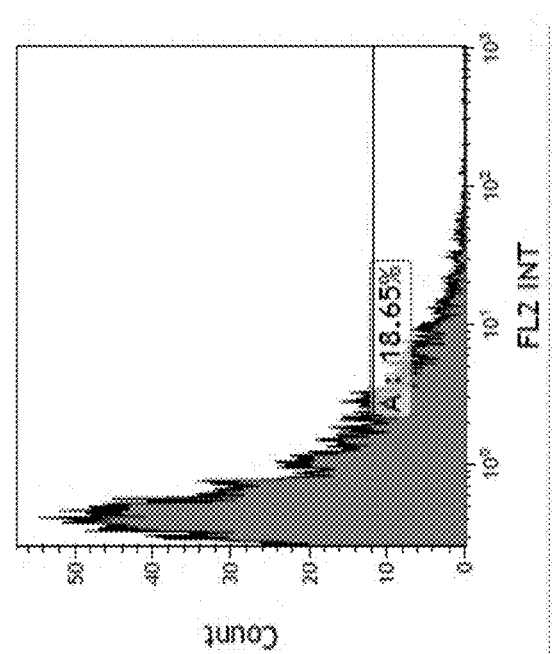

Osteogenic induction was evaluated by the osteogenic marker ALP, using FACS (FIGS. 16 A-B). Results show that cells cultivated in the dynamic HFR system had a higher level of ALP positive cells (33.23%, 16B) compared to the level of ALP positive cells (18.65%) of cells cultivated in the static system (16A).

Figure 17C:
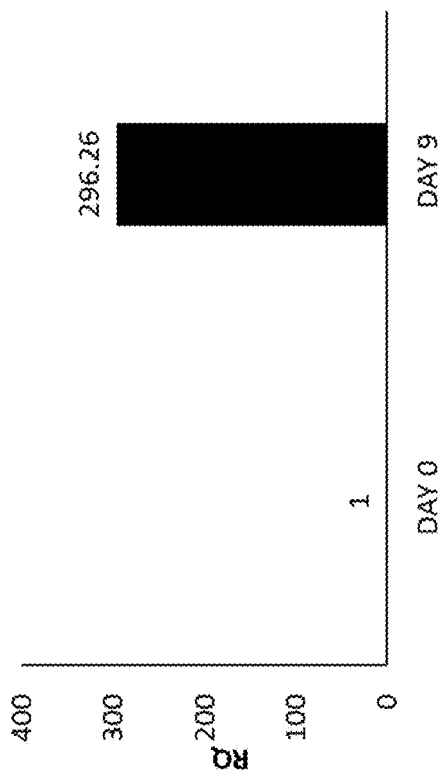
FIGS. 17A-D are bar graphs showing Real-Time PCR results of DLX5 expression at day 0 and day 9 in MSCs grown in a static system (A) or a dynamic system (B), and SP7 expression at day 0 and day 9 in MSCs grown in a static system (C) or a dynamic system (D)
Figure 17D:
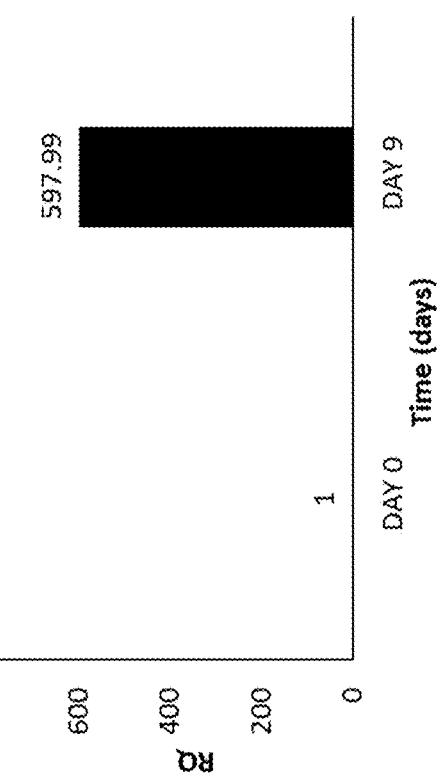
Figure 17A:
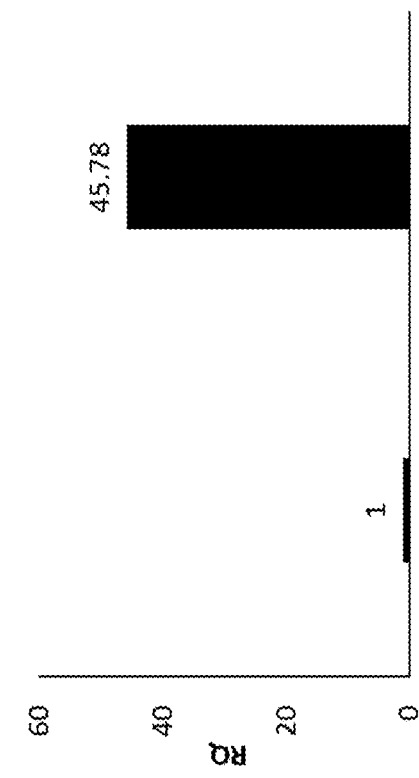
Figure 17B:
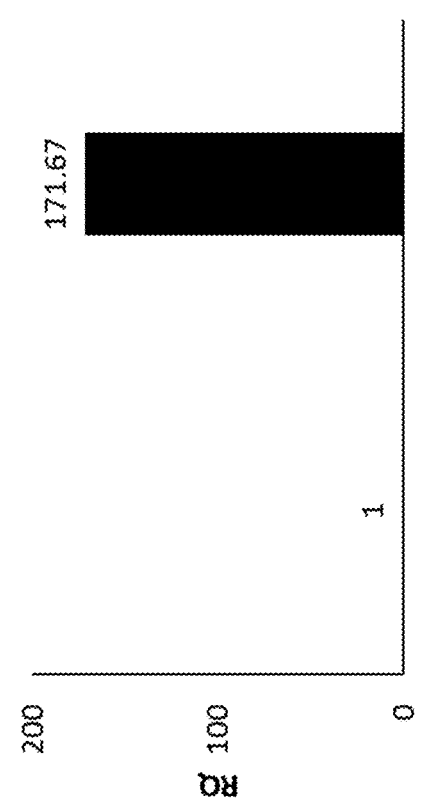
Figure 18B:
FIGS. 18A-B are photographs of Giemsa staining (A) and AC-LDL staining (B) of human adipose microvascular endothelial cells (HAMEC) grown in microcapillary reactor system.
Figure 18A:

Osteogenic differentiation was also evaluated using Real-Time PCR (FIGS. 17A-C). The RNA was extracted using the PureLink® RNA Mini Kit (Life technologies). TaqMan osteogenic primers (DLX5 and Osterix (SP7)) were used for Real-Time reactions preparation. The osteogenic genes expression, following 2 days of osteogenic induction (day 9 of cultivation), was compared to the osteogenic genes expression at HFR seeding day (day 0). Both dynamic and static growth conditions were evaluated. Real time PCR results demonstrated DLX5 and SP7 gene expression are elevated post osteogenic induction (day 9) relative to day 0, indicating for osteogenic induction in both systems, with higher expression in dynamic HFR system compared to static system.

c. Endothelial Cells (ECs) Growth on the Microcapillary Scaffold in Dynamic and Static Culturing Systems:

The ability of the microcapillary system to support Seeding and growth of Human Adipose Microvascular Endothelial Cells (HAMEC) inside the microcapillary tubes was tested as following: the growth system was built as was described before, but with single PCL tube. Before cell seeding, the tube was coated with fibronectin to allow adherence of endothelial cells onto the inner surface of the tube lumen. The sterile PCL tube was aseptically filled with fibronectin solution and rotated for one hour at 37° C. incubator to allow even coating with fibronectin. Subsequently, suspension of endothelial cells was prepared in Endothelial Cell Medium (ECM) (from ScienCell). To seed cells, the PCL tube was drained out of the fibronectin solution, and filled instead with the prepared suspension of endothelial cells. Cells were seeded at a density of $5 \times 10^5$ cells/cm$^2$, and the tube was filled in the appropriate volume of medium. ECM medium was also used to submerge the PCL tube to cover the outside surfaces and the tube was rotated for two hours at 37° C. incubator to allow even seeding of cells onto the inner surface of the tube. After two hour-cell-seeding, the PCL tube was opened from both sides and was connected to the dynamic system including peristaltic pump and aerated growth medium reservoir. The growth medium was circulated constantly as previously described. The medium flow was kept for 48 hours. Next, the tube was taken out of the incubator and washed twice with PBS and stained with Giemsa and visualized (FIG. 18A). Adequate cell coverage of the inner walls of the tubes is seen with characteristic cobble stone morphology. Moreover, the HAMECs retained their AC-LDL uptake capabilities (FIG. 18B) which points out that their biological functionality is intact.

Example 7

Figure 19A:
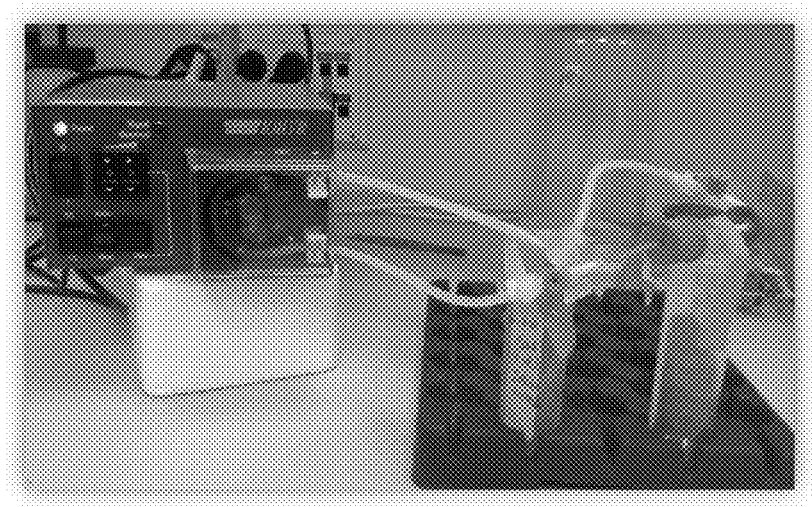
FIGS. 19A-B are a photograph (A) and a schematic illustration (B) of a microcapillary system for testing permeability to human plasma proteins.
Figure 19B:
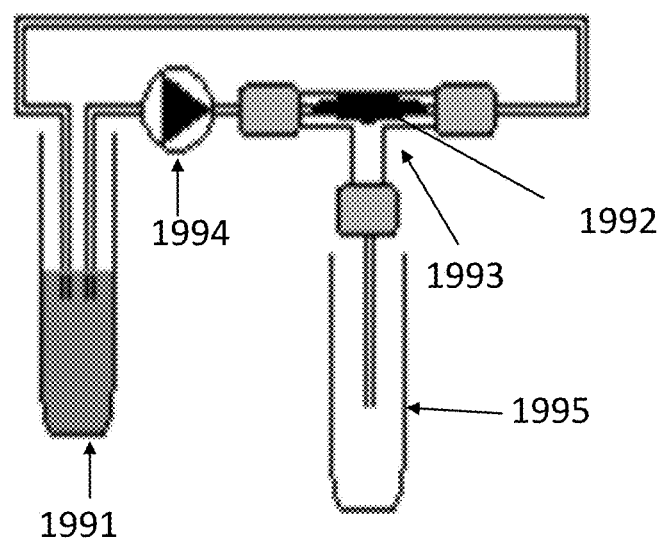
Figure 20A:
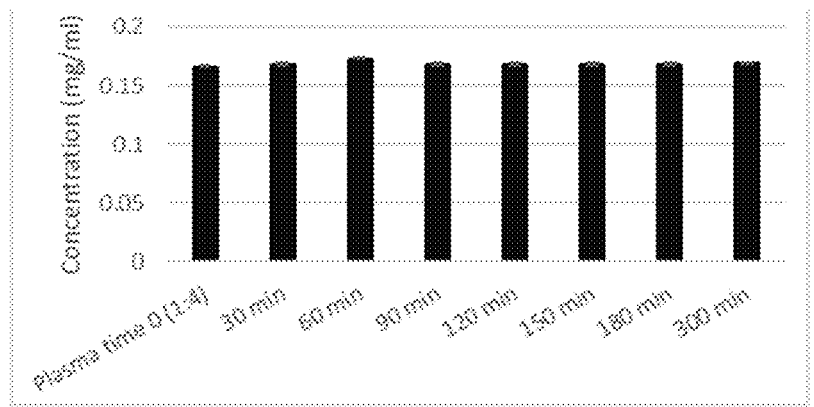
FIGS. 20A-C are bar graphs demonstrating concentrations of human serum albumin (A), IgG (B) and lysozyme (C) during the plasma circulation into the microcapillary construct.
Figure 20B:
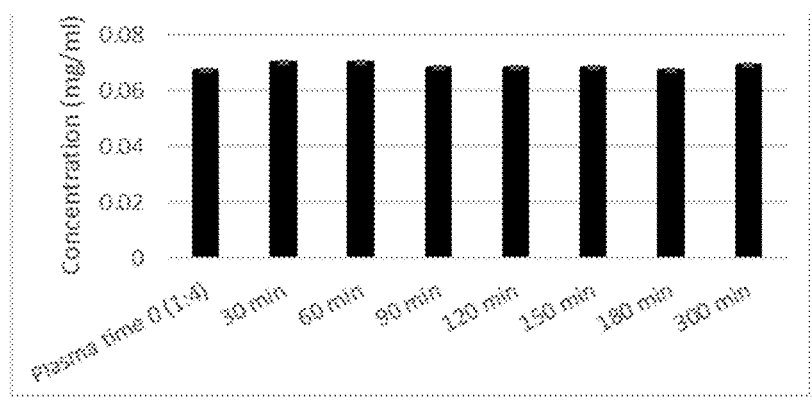
Figure 20C:
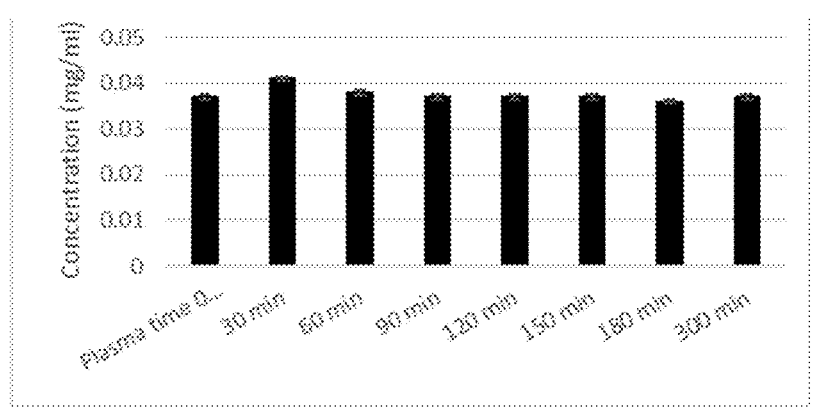

Demonstration of Human Plasma Protein Permeability Via the Microcapillary Scaffold, in Conditions that Mimic Blood Flow within the Scaffold The microcapillary construct permeability to human plasma proteins was tested using the system illustrated in FIGS. 19A-B. As demonstrated in the schematic illustration of FIG. 19B, a sample of human plasma (diluted 1:4) 1991 was streamed into the microcapillary system 1992 in a HFR vessel 1993 using a peristaltic pump 1994 in a circular manner. The microcapillary system wetted as planned and liquid droplets formed on the construct outer perimeter, the droplets were gathered using a collection tube 1995. Sampling the liquid gathered inside the collection tube was sampled every 30 min for 5 hr. Human serum albumin, IgG and lysozyme concentrations were determined in every sample (using IMPLEN's NanoPhotometer® P-Class) and were compared to the concentrations in the plasma before the experiment. Results demonstrate that the system is permeable to all tested proteins: human serum albumin (FIG. 20A), IgG (FIG. 20B) and Lysozyme (FIG. 20C). Further a constant wetting rate was observed meaning there is no plugging of the system with time.

Example 8

Standardization and Stability of the Microcapillary Scaffold

The electrospinning machine includes syringe that contains the polymer solution which is 12% polycaprolactone (PCL, Mw 80,000 Da) in an 80:20 (w/w) mixture of chloroform and dimethylformamide (DMF). The polymer syringe (5 ml BD plastic syringe) is driven by a syringe pump which is used to control the flow rate (1 ml/hour) of the polymer being ejected. The electrospinning machine also includes high voltage power supply which apply a fixed voltage of 15-20 kV to a metallic needle (21G) connected to the polymer syringe. The polymer solution (12% PCL) pass through the needle and is charged by the high voltage that is directly opposite to the surface tension of the polymer solution, leading to the elongation of the hemispherical surface of the solution at the tip of the syringe to form a conical shape known as "Taylor cone". Due to elongation and solvent evaporation, the charged jet forms randomly oriented nanofibers that are collected on a grounded metallic collector made of wire of 0.5 mm diameter, or tubes of 0.86 mm or 1.5 mm diameter.

Tubes of 0.5 mm diameter are the capillary-like tube and tubes of 0.86 mm and 1.5 mm diameter are the vein-like tube that is cut to two tubes and connected to both sides of the capillary-like tube.

The vasculature-like system for in vitro experiments is made of three PCL tubes of 0.5 mm (collection time 8 minutes, flow rate 1 ml/hour) which are connected together from both sides by PCL tubes of 1.5 mm (collection time 40 minutes, flow rate 1 ml/hour), which resemble an inlet and outlet grafts for media infusion into the construct. The three tubes are surrounded with pro-osteon particles that are dispersed in between and onto the PCL tubes and are kept in place by the PCL fibers.

Example 9

Demonstration of Microsurgery Technique Proof of Concept—for Transplantation of the Microcapillary Scaffold End to End in a Rat Model To provide compatibility between the diameters of the vein-like tube (inlet/outlet) and the rat femoral/artery vein, a vein-like tube having a diameter of 0.86 mm was produced, using a collector of 0.86 mm by the electrospinning technique. The adjustment in the vein diameter was done to overcome any incompatibility between the diameters of the vein-like tube (inlet/outlet) and the rat femoral/artery vein that can lead to blood leakage from the anastomosis site the vein-like tube diameter. In addition, the number of capillary-like tubes connected to the vein-like tubes was adjusted to two capillary-like PCL tubes of 0.5 mm. These two capillaries were surrounded by bone-inducing material (pro-osteon) and electrospun PCL fibers, and connected together to 0.86 mm vein-like tube in both sides using PCL solution as glue.

Figure 22A:
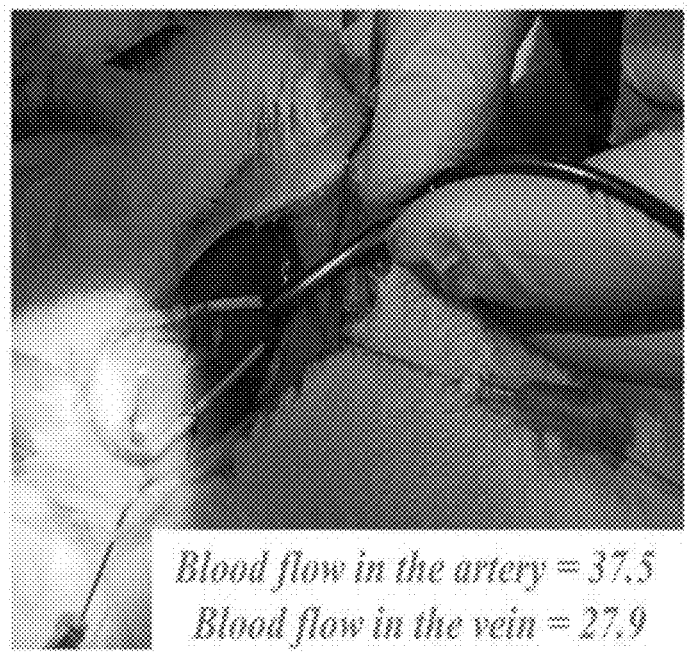
FIGS. 22A-B are photographs demonstrating the measurement of blood flow from artery to vein in the anastomosis site (A) and the measured value for blood flow in the artery as displayed on the laser flow meter (B)
Figure 22B:
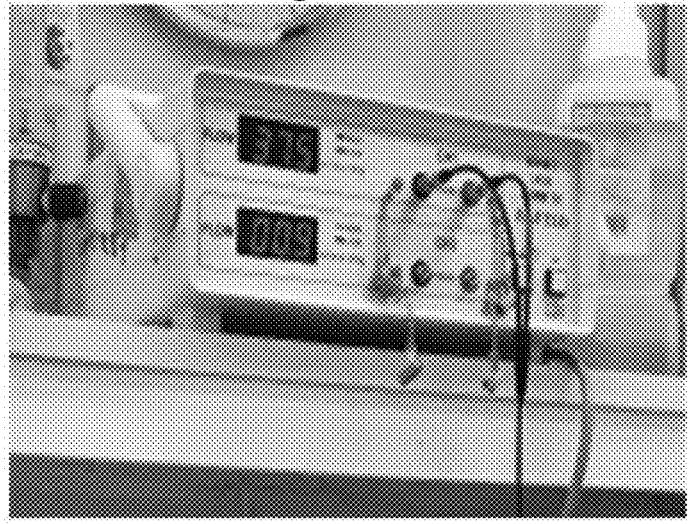

Next, the system was sterilized and transplanted in Sprague Dawley (SD) rat model using microsurgery technique. The vasculature-like system was fixated to the rat muscle tissue, then anastomosed to the femoral artery in one side and the femoral vein in the other one by 6-8 stitches in each side done with 10-0 Prolene microsurgical suture via "End to End" anastomosis (FIG. 21A-H). After finishing the anastomosis and releasing the clamps that held the artery and vein, no blood was leaked from the connection site. Using laser Doppler, the blood flow in the artery and vein was measured (FIG. 22A), demonstrating a blood flow through the vasculature-like system (FIG. 23). Later, the rat skin was stitched above the transplant and coated with polydine ointment to prevent any infections. After the surgery, the rat was examined for a week; and no pain was shown by the rat and it moved freely which mean that no damage was done to its limbs although it lost the main blood supply.

Figure 24:
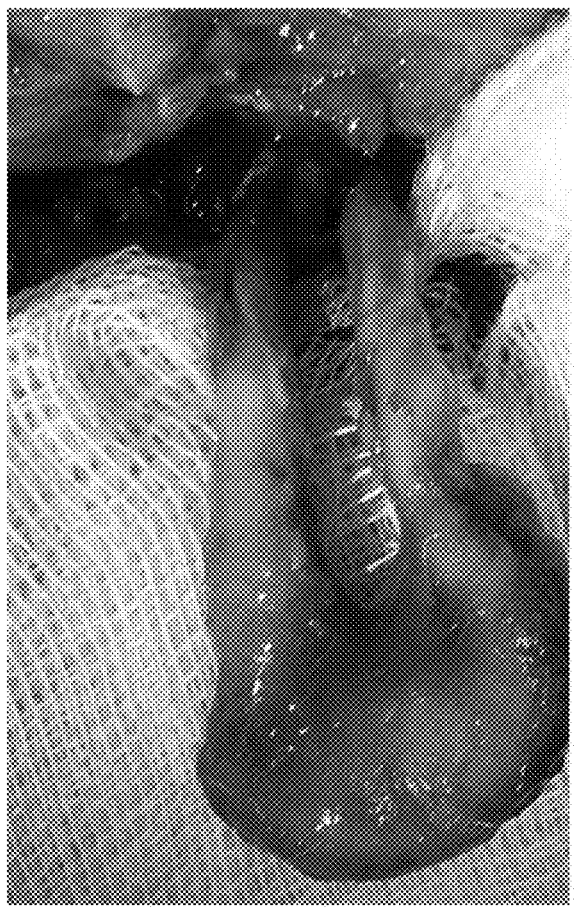
FIG. 24 vasculature-like system extracted 14 days following the transplantation.
Figure 25A:
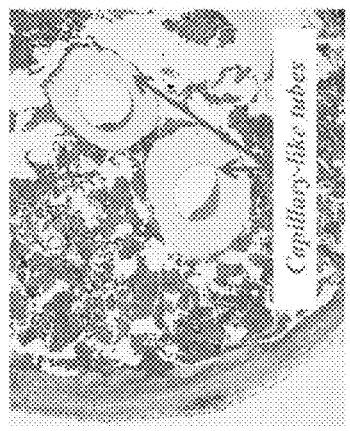
FIG. 25A-D are histological images magnified by ×10 (A) ×40 (B) ×60 (C) and ×100 (D) of the transplanted vasculature-like system extracted from the rats 14 days after the transplantation and stained by Hematoxylin & Eosin staining.
Figure 25C:
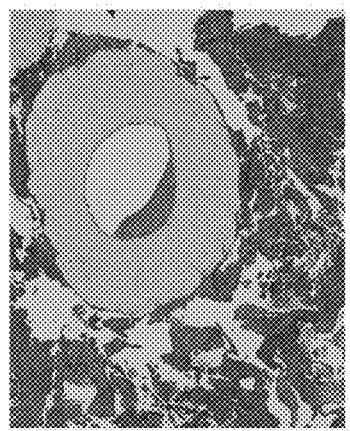
Figure 25B:
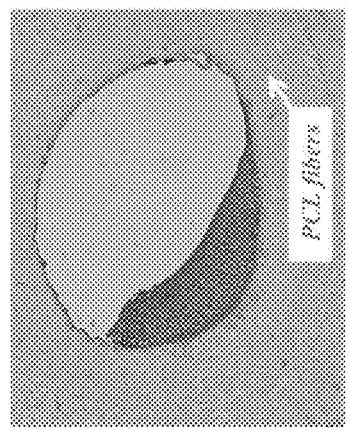
Figure 25D:
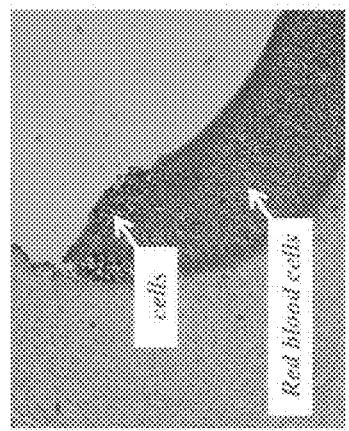

One day later, the rat was anesthetized and the stitches were cut of the skin in order to measure the blood flow through the femoral artery and vein. As demonstrated in FIGS. 23A-B the blood still flowed through the anastomosed vasculature-like system but it was reduced by 41-47% according to the laser Doppler (FIGS. 23C and 23D), probably as a result of blood clots. Two weeks later, the rat was sacrificed and the transplant was extracted (FIG. 24).

Next, the extracted transplants were fixated, Paraffin-embedded blocks were prepared and stained with Hematoxylin & Eosin. Histological analysis of the transplant showed that the scaffold structure is maintained, the fibers of PCL tubes were not destroyed and there is accumulation of cells into the capillary-like tubes (FIG. 25A-D).

Figure 26A:
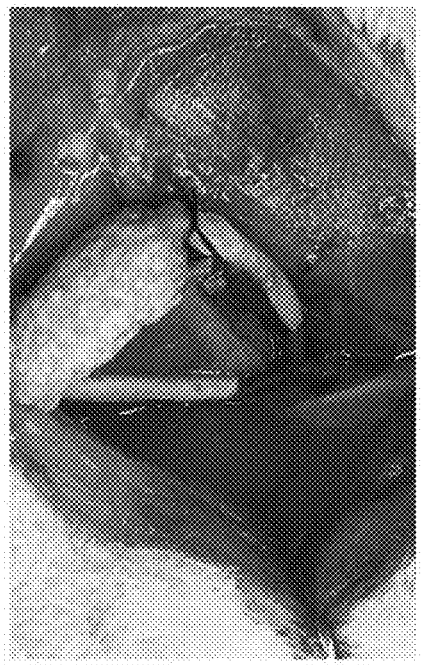
FIGS. 26A-D are photographs demonstrating the anastomosis of heparin-soaked scaffold to the femoral artery from one side (A) and the scaffold connected to femoral artery from one side and the femoral vein from the other side with no apparent leakage from the connection sites (B)
Figure 26B:
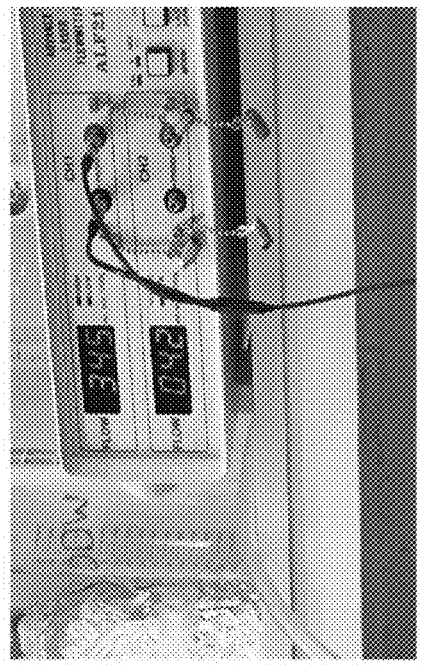
Figure 26C:
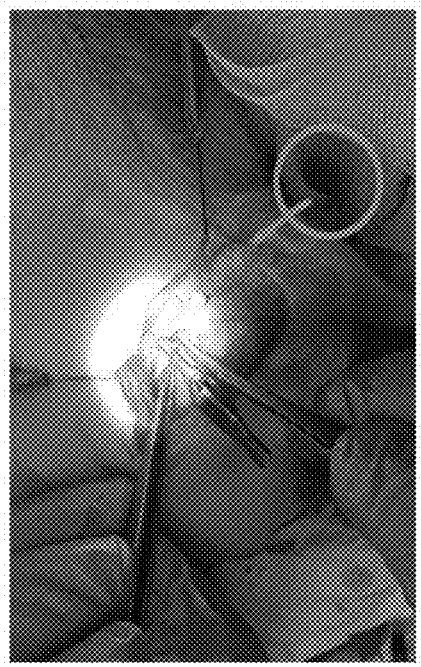
Figure 26D:
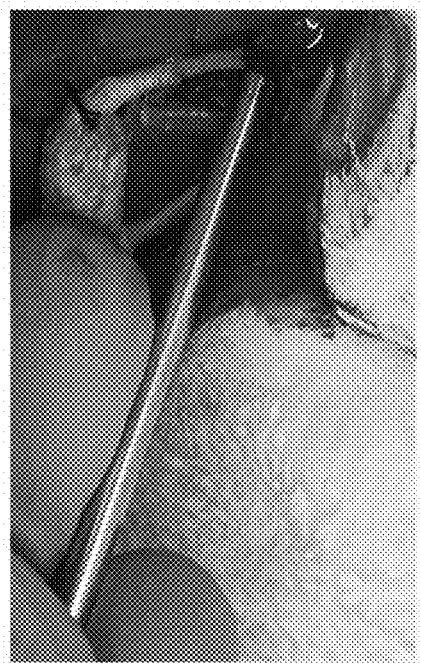

In order to prevent clotting inside the vasculature-like system during the surgery, the scaffold was soaked with phosphate buffered Saline (PBS), and 2 ml of Heparin were injected (5000 unit/ml) through it to be soaked with heparin. Next, the heparin-soaked scaffold was anastomosed to the femoral artery from one side, blood passage through the scaffold was examined by releasing the blocking clamp for seconds (FIG. 26A). Next, the other side was connected to the femoral vein. After releasing the clamps, the blood flowed through the scaffold without any leakage from the connection site (FIG. 26B). In addition, every rat was injected subcutaneously with 75 Units/kg of heparin after completing the surgery. Three weeks later, the rats were anesthetized; their blood flow through the transplants was measured (FIG. 26C), and the laser Doppler showed that although much improved, there is still a slight reduction in the blood flow (FIG. 26D).

In the following surgeries, in order to overcome any clotting that may occur in the transplant and reduce the blood flow through it; a daily dosage of 100 units/kg heparin was inject for a week after the transplantation. There was no bleeding as a result of heparin and the rats acted and moved normally.

Example 10

Calibrated Flow Rates

The flow rates were evaluated using a calibrated peristaltic pump and relevant blood flow rates obtained from the Literature. The pressure on the blood vessel wall is influence by the blood flow rate inside the blood vessels and this pressure in turn is the driving force for blood penetration throws the walls. As mention above, in the large blood vessels it is not desirable process, while in capillary it is necessary process for the cell nourish. Since the blood flow rate influence by the blood velocity and the cross section of the blood vessels, penetration tests should be evaluated in the relevant flow rates.

The peristaltic pump was calibrated in order to examine the range of its flow rate. Two pump rate were examined (high 100 rpm and low 11 rpm) and the coming out fluid volume was measured after defined time (20-75 minutes). Flow rate (Q) was calculated using Equation 2 (V—volume, t—time) and the flow velocity was measured using Equation 3 (v—velocity, A—area=$\pi r^2$).

$$Q\left(\frac{ml}{\sec}\right) = \frac{V(ml)}{t(\sec)} \quad \text{Equation 2}$$

$$v\left(\frac{cm}{\sec}\right) = \frac{Q(ml/\sec)}{A(cm^2)} \quad \text{Equation 3}$$

The results are shown in Table 1, while blood flow velocity in different types of blood vessels is demonstrated in Table 2. FIG. 8 shows the flow rate of the peristaltic pump in correlation with pump rate.

TABLE 1

Peristaltic pump calibration and flow rate calculation

| Volume (ml) | Time (min) | Flow Rate (ml/hr) |
|---|---|---|
| Pump Rate (90/10) = 100 rpm | | |
| 21 | 20 | 63.00 |
| 48 | 40 | 72.00 |
| 62 | 72 | 51.67 |
| Q (ml/hr) | Mean | 62 |
| | SD | 10 |
| Q (ml/sec) | | 0.017 |
| v (cm/sec) | | 0.152 |
| Pump Rate (10/1) = 11 rpm | | |
| 5 | 20 | 15.00 |
| 8 | 48 | 10.00 |
| 11 | 63.5 | 10.39 |
| Q (ml/hr) | Mean | 12 |
| | SD | 3 |
| Q (ml/sec) | | 0.003 |
| v (cm/sec) | | 0.029 |

TABLE 2

Peristaltic pump calibration and flow rate calculation

| Relation between blood flow velocity and total cross-section area in human[1] Type of blood vessels | Blood velocity in cm/s V (cm/s) | Vessel diameter D (cm) | cross-section area A (cm$^2$) | Blood flow rate Q (cm$^3$/sec) |
|---|---|---|---|---|
| Aorta | 40 | 2.5 | 4.91 | 196 |
| Capillary | 0.03[2] | 0.0008 | 0.000001 | 0.00000002 |
| Vein | 15 | 0.5 | 0.20 | 3 |
| Tube like Vain | 0.152 | 0.38 | 0.11 | 0.0172 |

Figure 27:
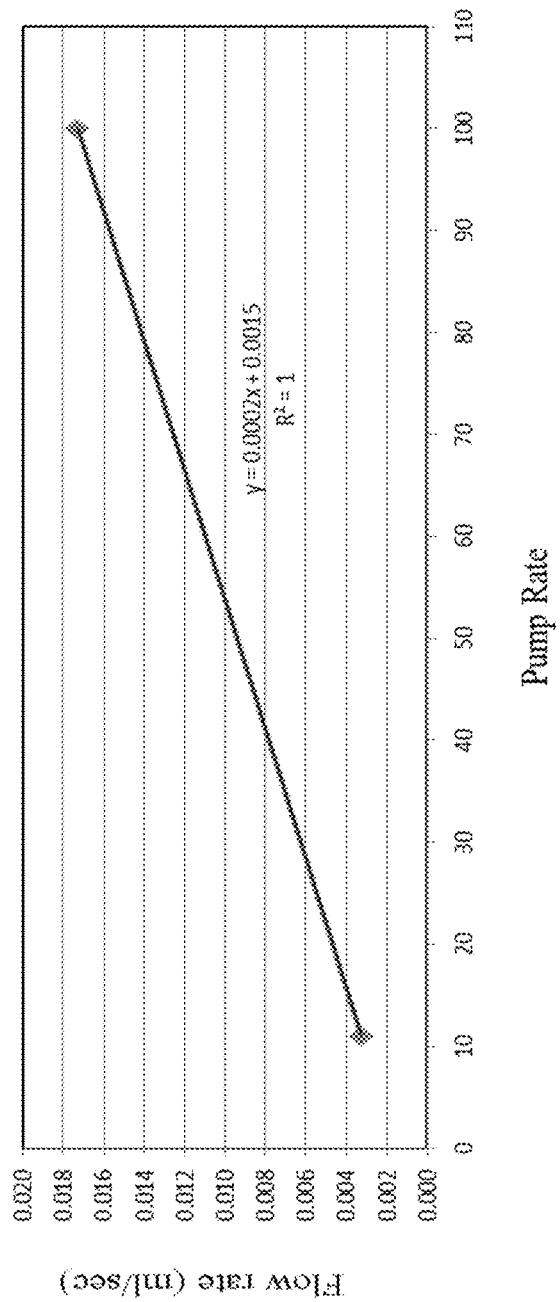
FIG. 27 is a graph plotting flow rate (milliliters/second) versus pump rate (RPM)

The fibers penetration levels of our tubes like vain and capillary fibers were evaluated based on fiber diameter, fiber thickness—depending on electrospinning duration—and PBS flow rate. Electrospun PCL tubes at different diameters and thickness were connected to the bioreactor system in order to examine their permeability (FIG. 27). The tube permeability was calculated using Equation 4.

$$\% \text{ permeability} = \frac{\text{leakage rate (ml/sec)}}{\text{Pump flow rate (ml/sec)}} \cdot 100\% \quad \text{Equation 4}$$

Figure 28:
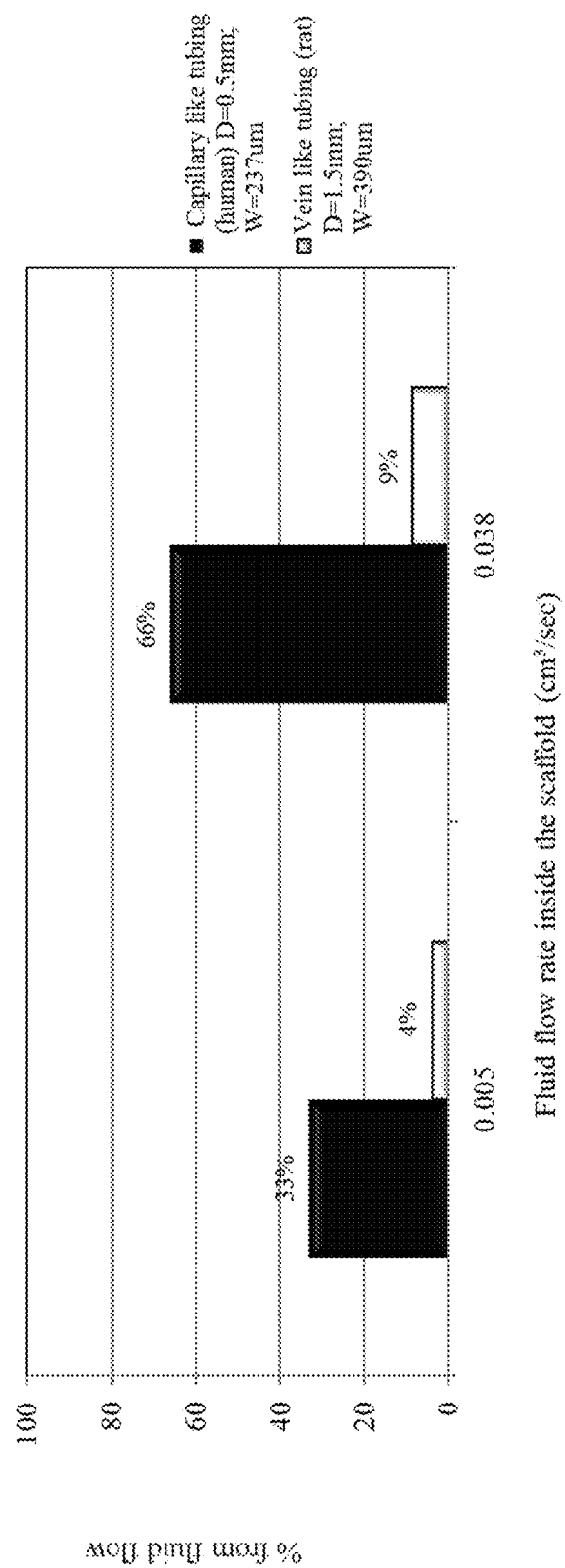
FIG. 28 is a bar graph showing fluid loss from the scaffold (presented as % of fluid flow) in capillary like tubes of human (diameter of 0.5 mm, width of 237 micrometers) and vein like tubes of rats (diameter of 1.5 mm, width of 390 micrometers) under a fluid flow rate of 0.005 $cm^3$/sec inside the scaffold compared to a fluid flow rate of 0.038 $cm^3$/sec inside the scaffold.

As demonstrated in the results below, tubes simulating veins were almost not penetrable. However, tubes simulating capillaries were 65% permeable. Moreover, it seems that ~40 minutes of electrospinning is sufficient to block almost completely the fiber wall. (FIG. 28).

What is claimed is:

1. A scaffold comprising:
at least one inlet tube;

at least one outlet tube;

a plurality of porous elongated microtubes, wherein each one of said porous elongated microtube has an inner diameter of 5-100 micrometers, wherein said plurality of elongated microtubes extend from said at least one inlet tube to said at least one outlet tube and is in fluid communication thereto;

a plurality of fibers having a diameter range of 0.5-10 micrometers, wherein said plurality of fibers is dispersed upon and in between a portion of each of said plurality of porous elongated microtubes; and a plurality of bioactive particles embedded in between said plurality of fibers.

2. The scaffold of claim 1, wherein the plurality of bioactive particles are kept in place by the plurality of fibers.

3. The scaffold of claim 1, wherein said bioactive particles have a range of 200-1500 micrometers in diameter.

4. The scaffold of claim 1, wherein said plurality of bioactive particles are one or more type of osteoconductive particles.

5. The scaffold of claim 4, wherein the one or more types of the osteoconductive particles are selected from the group consisting of: calcium carbonate, hydroxyapatite (HA), demineralized bone material, morselized bone graft, cortical cancellous allograft, cortical cancellous autograft, cortical cancellous xenograft, tricalcium phosphate, corraline mineral and calcium sulfate.

6. The scaffold of claim 4, wherein said particles comprise hydroxylapatite (HA) and calcium carbonate.

7. The scaffold of claim 1, wherein a portion of said scaffold is printed, molded, casted, polymerized, or electrospun.

8. The scaffold of claim 1, wherein at least one of said inlet tube, said outlet tube and said porous elongated microtubes are electrospun tubes.

9. The scaffold of claim 8, wherein said electrospun tubes comprise a polymer selected from the group consisting of: biodegradable polymers, non-biodegradable polymers and a combination thereof.

10. The scaffold of claim 9, wherein said polymer is selected from the group consisting of: polycaprolactone (PCL), polylactic acid (PLA), polyglycolic acid (PGA), and poly(Lactide-co-Glycolide) (PLGA), poly(orthoester), a poly(phosphazene), poly(or polycaprolactone, polyamide, polysaccharide, albumine and collagen.

11. The scaffold of claim 1, wherein said inlet tube and said outlet tube have a wall thickness range of 50-2,000 micrometers.

12. The scaffold of claim 1, wherein said plurality of porous elongated microtubes has a wall thickness range of 0.5-50 micrometers.

13. The scaffold of claim 1, wherein said inlet tube and said outlet tube have an inner diameter of range of 2,000-10,000 micrometers.

14. The scaffold of claim 1, wherein an average diameter of a pore of said plurality of porous elongated microtubes is 0.1-5 micrometers.

15. The scaffold of claim 1, further comprising at least one agent for promoting cell adhesion, colonization, proliferation and/or differentiation.

16. The scaffold of claim 1, further comprising at least one agent for promoting cell adhesion selected from the group consisting of: gelatin, fibrin, fibronectin and collagen.

17. The scaffold of claim 1, further comprising a plurality of cells seeded on and/or within said plurality of fibers.

18. The scaffold of claim 17, wherein said plurality of cells is selected from the group consisting of: adipose-derived stem cells, mesenchymal cells, mesenchymal stem cells, vascular smooth muscle cells, adipogenic cells, osteoprogenitors cells, osteoblasts, osteocytes, chondroblasts, chondrocytes and osteoclasts, endothelial progenitor cells, hematopoietic progenitor cells, micro vascular endothelial cells and macro vascular endothelial cells, beta cells, hepatocytes and a combination thereof.

* * * * *